United States Patent
Ma et al.

(10) Patent No.: US 12,340,996 B2
(45) Date of Patent: Jun. 24, 2025

(54) METHOD FOR RAPID ON-SITE DETECTION OF FENTANYL ANALOGS USING A MINIATURE MASS SPECTROMETER

(71) Applicant: Chinese Academy of Inspection and Quarantine, Beijing (CN)

(72) Inventors: Qiang Ma, Beijing (CN); Xiangyu Guo, Beijing (CN); Hua Bai, Beijing (CN); Wentao Li, Beijing (CN)

(73) Assignee: Chinese Academy of Inspection and Quarantine, Beijing (CN)

( * ) Notice: Subject to any disclaimer, the term of this patent is extended or adjusted under 35 U.S.C. 154(b) by 477 days.

(21) Appl. No.: 17/941,095

(22) Filed: Sep. 9, 2022

(65) Prior Publication Data

US 2023/0015987 A1    Jan. 19, 2023

Related U.S. Application Data

(63) Continuation of application No. PCT/CN2021/079645, filed on Mar. 9, 2021.

(30) Foreign Application Priority Data

Mar. 16, 2020   (CN) .......................... 202010181694.9

(51) Int. Cl.
H01J 49/00    (2006.01)
(52) U.S. Cl.
CPC ...... H01J 49/0013 (2013.01); H01J 49/0031 (2013.01)
(58) Field of Classification Search
CPC .... H01J 49/0013; H01J 49/0031; H01J 49/10; H01J 49/14; H01J 49/16; G01N 27/622; G01N 27/623
See application file for complete search history.

(56) References Cited

U.S. PATENT DOCUMENTS

2004/0166067 A1   8/2004   Watts et al.
2019/0227032 A1*  7/2019   Trimpin ............... G01N 27/622

FOREIGN PATENT DOCUMENTS

CN    103134847 A    6/2013
CN    103134848 A    6/2013
(Continued)

OTHER PUBLICATIONS

Zachary J. Devereaux et al., Matrix-Assisted Ionization on a Portable Mass Spectrometer: Analysis Directly from Biological and Synthetic Materials, Technical Note, Anal. Chem., 2016, 88, 22, 10831-10836.

(Continued)

*Primary Examiner* — David E Smith
*Assistant Examiner* — Hsien C Tsai
(74) *Attorney, Agent, or Firm* — Troutman Pepper Locke LLP; Tim Tingkang Xia, Esq.

(57) ABSTRACT

The present invention discloses a method for rapid on-site detection of fentanyl analogs using a miniature mass spectrometer, comprising the following steps: (1) selecting a spotting plate; (2) loading a sample: depositing the sample and 3-nitrobenzonitrile solution in acetonitrile on the spotting plate to form a crystalline mixture; (3) carrying out analysis and detection: setting the parameters of the miniature mass spectrometer, placing the crystalline mixture on the spotting plate in close proximity to the inlet of the miniature mass spectrometer, and facilitating the ionization of the crystalline mixture for the analysis and detection of fentanyl analogs. The method for rapid on-site detection of fentanyl analogs using a miniature mass spectrometer provided by the present invention requires no extraction solvent, no voltage, no laser, no gas, and the method is simple, rapid, and suitable for rapid on-site detection of fentanyl analogs.

4 Claims, 25 Drawing Sheets

(56) References Cited

FOREIGN PATENT DOCUMENTS

| CN | 104111283 A | 10/2014 |
|----|-------------|---------|
| CN | 104807877 A | 7/2015  |
| CN | 108732292 A | 11/2018 |
| CN | 10286187 A  | 9/2019  |
| CN | 111272860 A | 6/2020  |

OTHER PUBLICATIONS

China Patent Office, "Office Action", Aug. 17, 2022, China.
International Search Report of PCT/CN2021/079645, Jun. 8, 2021.
Alessandra M. Bruno et al., Balancing the utility and legality of implementing portable mass spectrometers coupled with ambient ionization in routine law enforcement activities, Analytical Methods, vol. 9, 2017.
Xiangyu Gui et al., Research Advances in Ambient Ionization and Miniature Mass Spectrometry, (non-official translation: Reviews and Progress in Analytical Chemistry), vol. 47, No. 3, 2017, pp. 335-346.

\* cited by examiner

METHOD FOR RAPID ON-SITE DETECTION OF FENTANYL ANALOGS USING A MINIATURE MASS SPECTROMETER

CROSS-REFERENCE TO RELATED APPLICATION

This application is a continuation application of International Patent Application No. PCT/CN2021/079645, filed on Mar. 9, 2021, which itself claims priority to and benefit of Chinese Patent Application No. 202010181694.9 filed on Mar. 16, 2020 in the State Intellectual Property Office of P. R. China. The disclosure of each of the above applications is incorporated herein by reference in its entirety.

FIELD OF THE INVENTION

The present invention relates to a method for detection of chemical substances, especially a method for rapid on-site detection of fentanyl analogs using a miniature mass spectrometer.

BACKGROUND OF THE INVENTION

Fentanyl is an opioid receptor agonist synthesized by a Belgian scientist named Paul Janssen in 1960, having a chemical name of N[1-(2-phenethyl)-4-piperidiny]-N-phenylpropionamide. With the analgesic effect 80 times than that of morphine, fentanyl is commonly used for anesthesia during and after surgery. Fentanyl analogs are formed by modification of the parent substance (fentanyl) and are composed of three parts: phenylalkyl, piperidinyl ring, and propylalkylamide. Fentanyl analogs include remifentanil, carfentanil, sufentanil, etc., the analgesic effect of which is normally higher than that of fentanyl. For example, the analgesic effect of carfentanil is 100 times than that of fentanyl and 10,000 times than that of morphine.

Fentanyl analogs have powerful analgesic effect, short onset time, and are easily accessible. However, their excessive use may lead to physical and mental dependence, respiratory depression, and even death. In recent years, the abuse of fentanyl and fentanyl analogs has continued worldwide, causing a large number of casualties and seriously impairing social stability. Within just four months from the end of 2015 to the beginning of 2016, Sweden reported seven deaths due to the overdose of fentanyl analogs; in the same year, five deaths were caused by overdose of fentanyl analogs in Ohio of USA. With the increasing number of deaths, the prevention and control of fentanyl analogs are urgent. On May 1, 2019, the Ministry of Public Security, National Health Commission, and State Food and Drug Administration of China listed fentanyl analogs in the Supplementary Catalogue of Controlled Varieties of Non-Medicinal Narcotic Drugs and Psychotropic Substances, implementing whole-class control for fentanyl analogs.

SUMMARY OF THE INVENTION

The technical problem to be solved by the present invention is to provide a simple, fast, and sustainable method that is suitable for rapid on-site detection of fentanyl analogs using a miniature mass spectrometer. The studies of the present invention include the investigations of the types of fentanyl analogs, ionization modes of chemical analytes, and detection conditions of ambient ionization and miniature mass spectrometer.

A method for rapid on-site detection of fentanyl analogs using a miniature mass spectrometer, comprising the following steps:

(1) selecting a spotting plate;
(2) loading a sample: depositing the sample and 3-nitrobenzonitrile solution in acetonitrile on the spotting plate to form a crystalline mixture;
(3) carrying out analysis and detection: setting the parameters of the miniature mass spectrometer, placing the crystalline mixture on the spotting plate in close proximity to the inlet of the miniature mass spectrometer, and facilitating the ionization of the crystalline mixture for the analysis and detection of fentanyl analogs;

wherein the sample includes powder, blood, and sweat; there are 49 kinds of fentanyl analogs, and the analysis parameters of the miniature mass spectrometer and limits of detection (LODs) in step (3) are shown in Table 1;

TABLE 1

The analysis parameters of the miniature mass spectrometer and limits of detection (LODs) for the 49 fentanyl analogs

| Fentanyl analogs | Ionization mode | m/z | RF/kHz | AC/kHz | CID-AC/kHz | CID-AC/Vpp | LOD/(μg/kg) |
|---|---|---|---|---|---|---|---|
| fentanyl | positive | 337 | 150-800 | 5-46 | 47 | 220 | 20 |
| para-flufentanyl | positive | 355 | 150-880 | 5-42 | 43 | 220 | 20 |
| meta-flufentanyl | positive | 355 | 150-860 | 5-43 | 44 | 220 | 20 |
| ortho-flufentanyl | positive | 355 | 150-860 | 5-42 | 43 | 210 | 20 |
| N-phenyl-N-[1-[2-(2-thienyl)ethyl]-4-piperidyl]propanamide | positive | 343 | 150-840 | 5-44 | 45 | 220 | 50 |
| acetylfentanyl | positive | 323 | 150-780 | 5-45 | 46 | 210 | 50 |
| N-(2-fluorophenyl)-N-(1-phenethylpiperidin-4-yl)acetamide | positive | 341 | 150-820 | 5-44 | 45 | 215 | 20 |
| N-(3-fluorophenyl)-N-(1-phenethylpiperidin-4-yl)acetamide | positive | 341 | 150-820 | 5-44 | 45 | 220 | 20 |
| N-(4-fluorophenyl)-N-[1-(2-phenylethyl)-4-piperidinyl]-acetamide | positive | 341 | 150-820 | 5-44 | 45 | 220 | 20 |
| butyrfentanyl | positive | 351 | 150-830 | 5-43 | 44 | 235 | 50 |
| isobutyryl fentanyl | positive | 351 | 150-840 | 5-42 | 43 | 222 | 50 |
| 4-fluorobutyrfentanyl | positive | 369 | 150-900 | 5-40 | 41 | 225 | 50 |
| meta-fluorobutyryl fentanyl | positive | 369 | 150-880 | 5-40 | 41 | 220 | 50 |
| N-(2-fluorophenyl)-N-(1-phenethylpiperidin-4-yl)butyramide | positive | 369 | 150-880 | 5-40 | 41 | 220 | 50 |
| para-fluoroisobutyrfentanyl | positive | 369 | 150-880 | 5-40 | 41 | 220 | 50 |
| cis-3-methylfentanyl | positive | 351 | 150-850 | 5-43 | 44 | 223 | 50 |

TABLE 1-continued

The analysis parameters of the miniature mass spectrometer and limits of detection (LODs) for the 49 fentanyl analogs

| Fentanyl analogs | Ionization mode | m/z | RF/kHz | AC/kHz | CID-AC/kHz | CID-AC/Vpp | LOD/(μg/kg) |
|---|---|---|---|---|---|---|---|
| trans-3-methylfentanyl | positive | 351 | 150-850 | 5-43 | 44 | 221 | 50 |
| alpha-methylfentanyl | positive | 351 | 150-850 | 5-43 | 44 | 220 | 50 |
| N-[1-[1-methyl-2-(2-thienyl)ethyl]-4-piperidyl]-N-phenylpropanamide | positive | 357 | 150-870 | 5-42 | 43 | 217 | 100 |
| cis-3-methylthiofentanyl | positive | 357 | 150-880 | 5-42 | 43 | 215 | 100 |
| 2-methoxy-N-phenyl-N-[1-(2-phenylethyl)-4-piperidinyl]-acetamide | positive | 353 | 150-840 | 5-43 | 44 | 210 | 20 |
| para-methoxy acetyl fentanyl | positive | 353 | 150-840 | 5-42 | 43 | 220 | 20 |
| N-(2-fluorophenyl)-N-(1-phenethylpiperidin-4-yl)acrylamide | positive | 353 | 150-820 | 5-43 | 44 | 215 | 20 |
| N-[1-(2-hydroxy-2-phenylethyl)-4-piperidyl]-N-phenylpropanamide | positive | 353 | 150-840 | 5-42 | 43 | 220 | 200 |
| norfentanyl | positive | 232 | 150-600 | 5-67 | 68 | 180 | 50 |
| acrylfentanyl | positive | 335 | 150-820 | 5-44 | 45 | 220 | 50 |
| methyl-4-(N-phenylpropionamido)-1-phenethylpiperidine-4-carboxylate | positive | 395 | 150-930 | 5-36 | 37 | 200 | 100 |
| furanylfentanyl | positive | 375 | 150-920 | 5-40 | 41 | 205 | 50 |
| valerylfentanyl | positive | 365 | 150-900 | 5-40 | 41 | 225 | 50 |
| ocfentanil | positive | 371 | 150-880 | 5-40 | 41 | 215 | 50 |
| remifentanil | positive | 377 | 150-940 | 5-39 | 40 | 180 | 200 |
| sufentanyl | positive | 387 | 150-950 | 5-37 | 38 | 190 | 100 |
| alfentanil | positive | 417 | 150-1000 | 5-34 | 35 | 200 | 200 |
| N-phenyl-N-(1-phenethylpiperidin-4-yl)tetrahydrofuran-2-carboxamide | positive | 379 | 150-940 | 5-38 | 39 | 205 | 50 |
| heptanoyl fentanyl | positive | 394 | 150-920 | 5-36 | 37 | 225 | 50 |
| phenyl fentanyl | positive | 385 | 150-950 | 5-38 | 39 | 210 | 20 |
| hexanoyl fentanyl | positive | 380 | 150-940 | 5-38 | 39 | 230 | 50 |
| N-phenyl-N-(1-(2-(thiophen-2-yl)ethyl)piperidin-4-yl)acetamide | positive | 329 | 150-800 | 5-45 | 46 | 215 | 100 |
| N-(1-(2-hydroxy-2-(thiophen-2-yl)ethyl)piperidin-4-yl)-N-phenylpropanamide | positive | 359 | 150-890 | 5-41 | 42 | 213 | 200 |
| meta-fluoro methoxyacetyl fentanyl | positive | 371 | 150-890 | 5-40 | 41 | 200 | 50 |
| acetyl-alpha-methylfentanyl | positive | 337 | 150-800 | 5-44 | 45 | 226 | 20 |
| para-methoxy methoxyacetyl fentanyl | positive | 383 | 150-910 | 5-38 | 39 | 210 | 50 |
| beta-hydroxy-3-methylfentanyl | positive | 367 | 150-900 | 5-40 | 41 | 225 | 50 |
| para-methoxy acryl fentanyl | positive | 365 | 150-900 | 5-40 | 41 | 220 | 50 |
| para-methoxy tetrahydrofuran | positive | 409 | 150-920 | 5-35 | 36 | 210 | 20 |
| cyclopentyl fentanyl | positive | 378 | 150-890 | 5-39 | 40 | 210 | 50 |
| thiophene fentanyl | positive | 392 | 150-920 | 5-37 | 38 | 210 | 50 |
| 1-phenethyl-4-piperidone | positive | 204 | 150-500 | 5-76 | 77 | 220 | 20 |
| 1-phenethyl-N-phenylpiperidin-4-amine | positive | 281 | 150-670 | 5-55 | 56 | 230 | 20 | wherein the spotting plate is a triangular paper substrate.

According to the method for rapid on-site detection of fentanyl analogs using a miniature mass spectrometer, wherein: step (2) specifically comprises the following steps: transferring 1-3 μL of liquid sample or 1-3 μg of powder sample to the spotting plate, depositing 5-10 μL of the 3-nitrobenzonitrile solution in acetonitrile at a concentration of 100 μg/μL on the sample, and exposing to air for 10-30 seconds to form a crystalline mixture.

According to the method for rapid on-site detection of fentanyl analogs using a miniature mass spectrometer, wherein: in step (3), the crystalline mixture on the spotting plate was placed in close proximity to the inlet of the miniature mass spectrometer for 1-5 seconds, and the crystalline mixture was expected to produce charged particles upon sublimation due to the intrinsic vacuum at the inlet aperture of the miniature mass spectrometer.

According to the method for rapid on-site detection of fentanyl analogs using a miniature mass spectrometer, wherein: the base and height of the triangular paper substrate are 1 cm and 1.5 cm, respectively.

The difference between the method for rapid on-site detection of fentanyl analogs using a miniature mass spectrometer of the present invention and the prior art lies in that: the method for rapid on-site detection of fentanyl analogs using a miniature mass spectrometer provided by the present invention requires no extraction solvent, no voltage, no laser, no gas, and the method is simple, rapid, and suitable for rapid on-site detection of fentanyl analogs.

The inventiveness and advantages of the present invention are as follows:

1. For the first time, the present invention proposes a method combining matrix-assisted ionization and miniature mass spectrometry for rapid on-site detection of fentanyl analogs in suspicious powders or unknown liquids and the detection time is short;
2. The present invention does not need the uses of extraction solvent, voltage, laser or gas;
3. The types of samples involved in the present invention include: powder, blood, urine, sweat, etc.
4. The substances involved in the present invention include: 49 kinds of fentanyl analogs.

The method for rapid on-site detection of fentanyl analogs using a miniature mass spectrometer according to the present invention will be further described below with reference to the accompanying drawings.

BRIEF DESCRIPTION OF THE DRAWINGS

Additional objectives, functions, and advantages of the present invention will be set forth in the description of embodiments which follow, with reference to the accompanying drawings in which.

DETAILED DESCRIPTION OF THE INVENTION

1. Apparatus and Materials

Figure 1:
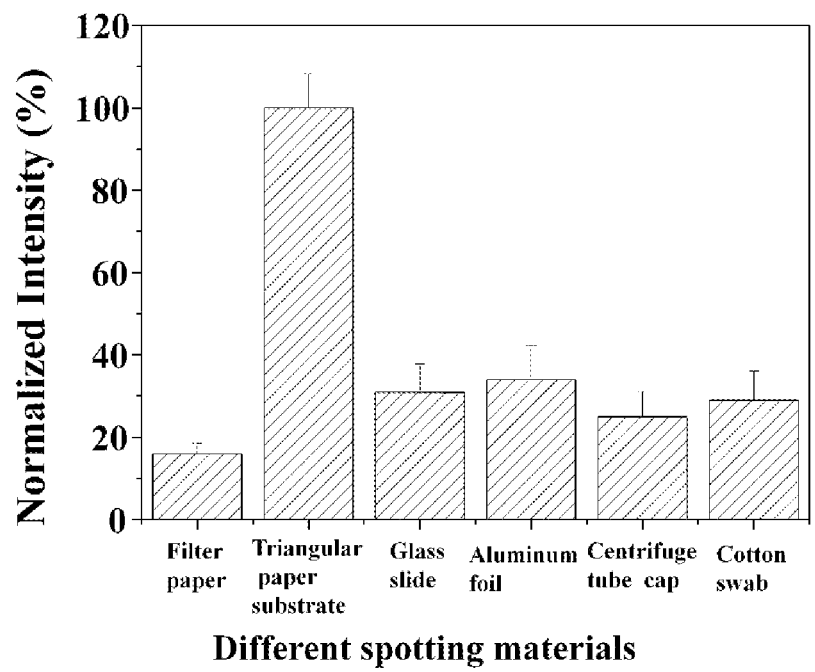
FIG. 1 is the schematic diagram of the selection of an optimal spotting plate according to the present invention.

Mini β miniature mass spectrometer: PURSPEC Technologies (Beijing, China). 3-nitrobenzonitrile, CAS number 619-24-9, molecular formula $C_7H_4N_2O_2$, and average molecular weight 148.12 g/mol.

2. Analysis and Detection Method

A method for rapid on-site detection of fentanyl analogs in suspicious powder or liquid samples using a miniature mass spectrometer includes the following steps:

(1) selecting a spotting plate: choosing a triangular paper substrate as the spotting plate, with a base of 1 cm and a height of 1.5 cm;

(2) loading a sample: loading 1-3 μL of liquid sample (or 1-3 μg of powder sample) to a tip of the triangular paper substrate, adding 5-10 μL of the 3-nitrobenzonitrile solution in acetonitrile on the spotting plate, and exposing to air for 10-30 seconds to form a crystalline mixture of the sample and 3-nitrobenzonitrile;

(3) carrying out analysis and detection: setting the parameters of the miniature mass spectrometer, placing the crystalline mixture on the spotting plate in close proximity to the inlet of the miniature mass spectrometer for 1-5 seconds, and facilitating the ionization of the crystalline mixture for the analysis and detection of fentanyl analogs.

There are 49 kinds of fentanyl analogs, and analysis parameters of the miniature mass spectrometer and LODs are as shown in Table 1;

TABLE 1

The analysis parameters of the miniature mass spectrometer and limits of detection (LODs) for the 49 fentanyl analogs

| Fentanyl analogs | Ionization mode | m/z | RF/kHz | AC/kHz | CID-AC/kHz | CID-AC/Vpp | LOD/(μg/kg) |
|---|---|---|---|---|---|---|---|
| fentanyl | positive | 337 | 150-800 | 5-46 | 47 | 220 | 20 |
| para-flufentanyl | positive | 355 | 150-880 | 5-42 | 43 | 220 | 20 |
| meta-flufentanyl | positive | 355 | 150-860 | 5-43 | 44 | 220 | 20 |
| ortho-flufentanyl | positive | 355 | 150-860 | 5-42 | 43 | 210 | 20 |
| N-phenyl-N-[1-[2-(2-thienyl)ethyl]-4-piperidyl]propanamide | positive | 343 | 150-840 | 5-44 | 45 | 220 | 50 |
| acetylfentanyl | positive | 323 | 150-780 | 5-45 | 46 | 210 | 50 |
| N-(2-fluorophenyl)-N-(1-phenethylpiperidin-4-yl)acetamide | positive | 341 | 150-820 | 5-44 | 45 | 215 | 20 |
| N-(3-fluorophenyl)-N-(1-phenethylpiperidin-4-yl)acetamide | positive | 341 | 150-820 | 5-44 | 45 | 220 | 20 |
| N-(4-fluorophenyl)-N-[1-(2-phenylethyl)-4-piperidinyl]-acetamide | positive | 341 | 150-820 | 5-44 | 45 | 220 | 20 |
| butyrfentanyl | positive | 351 | 150-830 | 5-43 | 44 | 235 | 50 |
| isobutyryl fentanyl | positive | 351 | 150-840 | 5-42 | 43 | 222 | 50 |
| 4-fluorobutyrfentanyl | positive | 369 | 150-900 | 5-40 | 41 | 225 | 50 |
| meta-fluorobutyryl fentanyl | positive | 369 | 150-880 | 5-40 | 41 | 220 | 50 |
| N-(2-fluorophenyl)-N-(1-phenethylpiperidin-4-yl)butyramide | positive | 369 | 150-880 | 5-40 | 41 | 220 | 50 |
| para-fluoroisobutyrfentanyl | positive | 369 | 150-880 | 5-40 | 41 | 220 | 50 |
| cis-3-methylfentanyl | positive | 351 | 150-850 | 5-43 | 44 | 223 | 50 |
| trans-3-methylfentanyl | positive | 351 | 150-850 | 5-43 | 44 | 221 | 50 |
| alpha-methylfentanyl | positive | 351 | 150-850 | 5-43 | 44 | 220 | 50 |
| N-[1-[1-methyl-2-(2-thienyl)ethyl]-4-piperidyl]-N-phenylpropanamide | positive | 357 | 150-870 | 5-42 | 43 | 217 | 100 |
| cis-3-methylthiofentanyl | positive | 357 | 150-880 | 5-42 | 43 | 215 | 100 |
| 2-methoxy-N-phenyl-N-[1-(2-phenylethyl)-4-piperidinyl]-acetamide | positive | 353 | 150-840 | 5-43 | 44 | 210 | 20 |
| para-methoxy acetyl fentanyl | positive | 353 | 150-840 | 5-42 | 43 | 220 | 20 |
| N-(2-fluorophenyl)-N-(1-phenethylpiperidin-4-yl)acrylamide | positive | 353 | 150-820 | 5-43 | 44 | 215 | 20 |
| N-[1-(2-hydroxy-2-phenylethyl)-4-piperidyl]-N-phenylpropanamide | positive | 353 | 150-840 | 5-42 | 43 | 220 | 200 |
| norfentanyl | positive | 232 | 150-600 | 5-67 | 68 | 180 | 50 |
| acrylfentanyl | positive | 335 | 150-820 | 5-44 | 45 | 220 | 50 |
| methyl-4-(N-phenylpropionamido)-1-phenethylpiperidine-4-carboxylate | positive | 395 | 150-930 | 5-36 | 37 | 200 | 100 |
| furanylfentanyl | positive | 375 | 150-920 | 5-40 | 41 | 205 | 50 |
| valerylfentanyl | positive | 365 | 150-900 | 5-40 | 41 | 225 | 50 |
| ocfentanil | positive | 371 | 150-880 | 5-40 | 41 | 215 | 50 |
| remifentanil | positive | 377 | 150-940 | 5-39 | 40 | 180 | 200 |
| sufentanyl | positive | 387 | 150-950 | 5-37 | 38 | 190 | 100 |
| alfentanil | positive | 417 | 150-1000 | 5-34 | 35 | 200 | 200 |
| N-phenyl-N-(1-phenethylpiperidin-4-yl)tetrahydrofuran-2-carboxamide | positive | 379 | 150-940 | 5-38 | 39 | 205 | 50 |
| heptanoyl fentanyl | positive | 394 | 150-920 | 5-36 | 37 | 225 | 50 |
| phenyl fentanyl | positive | 385 | 150-950 | 5-38 | 39 | 210 | 20 |
| hexanoyl fentanyl | positive | 380 | 150-940 | 5-38 | 39 | 230 | 50 |
| N-phenyl-N-(1-(2-(thiophen-2-yl)ethyl)piperidin-4-yl)acetamide | positive | 329 | 150-800 | 5-45 | 46 | 215 | 100 |
| N-(1-(2-hydroxy-2-(thiophen-2-yl)ethyl)piperidin-4-yl)-N-phenylpropanamide | positive | 359 | 150-890 | 5-41 | 42 | 213 | 200 |
| meta-fluoro methoxyacetyl fentanyl | positive | 371 | 150-890 | 5-40 | 41 | 200 | 50 |
| acetyl-alpha-methylfentanyl | positive | 337 | 150-800 | 5-44 | 45 | 226 | 20 |
| para-methoxy methoxyacetyl fentanyl | positive | 383 | 150-910 | 5-38 | 39 | 210 | 50 |
| beta-hydroxy-3-methylfentanyl | positive | 367 | 150-900 | 5-40 | 41 | 225 | 50 |
| para-methoxy acryl fentanyl | positive | 365 | 150-900 | 5-40 | 41 | 220 | 50 |
| para-methoxy tetrahydrofuran | positive | 409 | 150-920 | 5-35 | 36 | 210 | 20 |
| cyclopentyl fentanyl | positive | 378 | 150-890 | 5-39 | 40 | 210 | 50 |
| thiophene fentanyl | positive | 392 | 150-920 | 5-37 | 38 | 210 | 50 |
| 1-phenethyl-4-piperidone | positive | 204 | 150-500 | 5-76 | 77 | 220 | 20 |
| 1-phenethyl-N-phenylpiperidin-4-amine | positive | 281 | 150-670 | 5-55 | 56 | 230 | 20 |

TABLE 2

The information on the 49 fentanyl analogs

| Name | molecular formula | molecular weight |
|---|---|---|
| fentanyl hydrochloride | $C_{22}H_{28}N_2O \bullet HCl$ | 372.94 |
| para-fluorofentanyl hydrochloride | $C_{22}H_{27}FN_2O \bullet HCl$ | 390.93 |
| meta-fluorofentanyl hydrochloride | $C_{22}H_{27}FN_2O \bullet HCl$ | 390.93 |
| ortho-fluorofentanyl hydrochloride | $C_{22}H_{27}FN_2O \bullet HCl$ | 390.93 |
| N-phenyl-N-[1-[2-(2-thienyl)ethyl]-4-piperidyl]propanamide hydrochloride | $C_{20}H_{26}N_2OS \bullet HCl$ | 378.96 |
| acetyl fentanyl | $C_{21}H_{26}N_2O$ | 322.44 |
| N-(2-fluorophenyl)-N-(1-phenethylpiperidin-4-yl)acetamide hydrochloride | $C_{21}H_{25}FN_2O \bullet HCl$ | 376.90 |
| N-(3-fluorophenyl)-N-(1-phenethylpiperidin-4-yl)acetamide hydrochloride | $C_{21}H_{25}FN_2O \bullet HCl$ | 376.90 |
| N-(4-fluorophenyl)-N-[1-(2-phenylethyl)-4-piperidinyl]-acetamide, hydrochloride | $C_{21}H_{25}FN_2O \bullet HCl$ | 376.90 |
| butyrfentanyl hydrochloride | $C_{23}H_{30}N_2O \bullet HCl$ | 386.96 |
| isobutyryl fentanyl | $C_{23}H_{30}N_2O$ | 350.50 |
| 4-fluorobutyrfentanyl | $C_{23}H_{29}FN_2O$ | 368.49 |
| meta-fluorobutyryl fentanyl hydrochloride | $C_{23}H_{29}FN_2O \bullet HCl$ | 404.95 |
| N-(2-fluorophenyl)-N-(1-phenethylpiperidin-4-yl)butyramide hydrochloride hydrate | $C_{23}H_{29}FN_2O \bullet HCl \bullet H_2O$ | 422.97 |
| p-fluoroisobutyrfentanyl | $C_{23}H_{29}FN_2O \bullet HCl$ | 404.95 |
| cis-3-methylfentanyl hydrochloride | $C_{23}H_{30}N_2O \bullet HCl$ | 386.96 |
| trans-3-methylfentanyl hydrochloride | $C_{23}H_{30}N_2O \bullet HCl$ | 386.96 |
| alpha-methylfentanyl hydrochloride | $C_{23}H_{30}N_2O \bullet HCl$ | 386.96 |
| N-[1-[1-methyl-2-(2-thienyl)ethyl]-4-piperidyl]-N-phenylpropanamide hydrochloride | $C_{21}H_{28}N_2OS \bullet HCl$ | 392.99 |
| cis-3-methylthiofentanyl hydrochloride | $C_{21}H_{28}N_2OS \bullet HCl$ | 392.99 |
| 2-methoxy-N-phenyl-N-[1-(2-phenylethyl)-4-piperidinyl]-acetamide hydrochloride | $C_{22}H_{28}N_2O_2 \bullet HCl$ | 388.94 |
| para-methoxy Acetyl fentanyl hydrochloride hemihydrate | $C_{22}H_{28}N_2O_2 \bullet HCl \bullet 0.5H_2O$ | 397.94 |
| N-(2-fluorophenyl)-N-(1-phenethylpiperidin-4-yl)acrylamide hydrochloride | $C_{22}H_{25}FN_2O \bullet HCl$ | 388.91 |
| N-[1-(2-hydroxy-2-phenylethyl)-4-piperidyl]-N-phenylpropanamide hydrochloride | $C_{22}H_{28}N_2O_2 \bullet HCl$ | 388.94 |
| norfentanyl hydrochloride hydrate | $C_{14}H_{20}N_2O \bullet HCl \bullet H_2O$ | 286.80 |
| acrylfentanyl | $C_{22}H_{26}N_2O$ | 334.46 |
| methyl-4-(N-phenylpropionamido)-1-phenethylpiperidine-4-carboxylate hydrochloride | $C_{24}H_{30}N_2O_3 \bullet HCl$ | 430.97 |
| furanylfentanyl | $C_{24}H_{26}N_2O_2$ | 374.48 |
| valerylfentanyl | $C_{24}H_{32}N_2O$ | 364.53 |
| ocfentanil | $C_{22}H_{27}FN_2O_2$ | 370.46 |
| remifentanil hydrochloride | $C_{20}H_{28}N_2O_5 \bullet HCl$ | 412.91 |
| sufentanyl | $C_{22}H_{30}N_2O_2S$ | 386.55 |
| alfentanil hydrochloride | $C_{21}H_{32}N_6O_3 \bullet HCl$ | 452.98 |
| N-phenyl-N-(1-phenethylpiperidin-4-yl)tetrahydrofuran-2-carboxamide hydrochloride hemihydrate | $C_{24}H_{30}N_2O_2 \bullet HCl \bullet 0.5H_2O$ | 423.98 |
| heptanoyl fentanyl hydrochloride | $C_{26}H_{36}N_2O \bullet HCl$ | 429.05 |
| phenyl fentanyl hydrochloride | $C_{26}H_{28}N_2O \bullet HCl$ | 420.98 |
| hexanoyl fentanyl hydrochloride | $C_{25}H_{34}N_2O \bullet HCl$ | 415.02 |
| N-phenyl-N-(1-(2-(thiophen-2-yl)ethyl)piperidin-4-yl)acetamide hydrochloride | $C_{19}H_{24}N_2OS \bullet HCl$ | 364.93 |
| N-(1-(2-hydroxy-2-(thiophen-2-yl)ethyl)piperidin-4-yl)-N-phenylpropanamide hydrochloride | $C_{20}H_{26}N_2O_2S \bullet HCl$ | 394.96 |
| meta-fluoro Methoxyacetyl fentanyl hydrochloride | $C_{22}H_{27}FN_2O_2 \bullet HCl$ | 406.93 |
| acetyl-alpha-methylfentanyl hydrochloride | $C_{22}H_{28}N_2O \bullet HCl$ | 372.94 |
| para-methoxy methoxyacetyl fentanyl hydrochloride | $C_{23}H_{30}N_2O_3 \bullet HCl$ | 418.96 |
| beta-hydroxy-3-methylfentanyl hydrochloride | $C_{23}H_{30}N_2O_2 \bullet HCl$ | 402.96 |
| para-methoxy acryl fentanyl hydrochloride | $C_{23}H_{28}N_2O_2 \bullet HCl$ | 400.95 |
| para-methoxy tetrahydrofuran fentanyl | $C_{25}H_{32}N_2O_3$ | 408.54 |
| cyclopentyl fentanyl hydrochloride | $C_{25}H_{32}N_2O \bullet HCl$ | 412.99 |
| thiophene fentanyl hydrochloride | $C_{24}H_{26}N_2OS \bullet HCl$ | 427.00 |
| 1-phenethyl-4-piperidone | $C_{13}H_{17}NO$ | 203.28 |
| 1-phenethyl-N-phenylpiperidin-4-amine dihydrochloride hydrate | $C_{19}H_{24}N_2 \bullet 2HCl \bullet H_2O$ | 371.35 |

Note:
Part of the 49 fentanyl analogs exist in the form of hydrochloride or hydrated hydrochloride.

A method for the detection of fentanyl in blood:

The experimental protocols described in the following embodiments are conventional methods unless otherwise specified. The reagents and materials can be obtained from commercial sources unless otherwise specified. The reference standards of fentanyl analogs were purchased from Shanghai Yuansi Biaowu Technology Co., Ltd.

Step 1: Preparation of Positive Sample

A standard solution of the fentanyl was added to the artificial blood. Positive artificial blood sample was prepared by adding 10 μL of the standard solution of fentanyl at a concentration of 100 μg/μL to 1 mL of artificial blood.

Step 2: Sample Deposition

Aliquots of 2 μL of positive sample were deposited onto the tip of the triangular paper substrate, 6 μL of the 3-nitrobenzonitrile solution in acetonitrile at a concentration of 100 μg/μLt (5 mg of 3-nitrobenzonitrile solid dissolved in 50 μL acetonitrile) was deposited, and the mixture was allowed to expose to air for 30 seconds.

Step 3: Ambient Ionization

Figure 2:
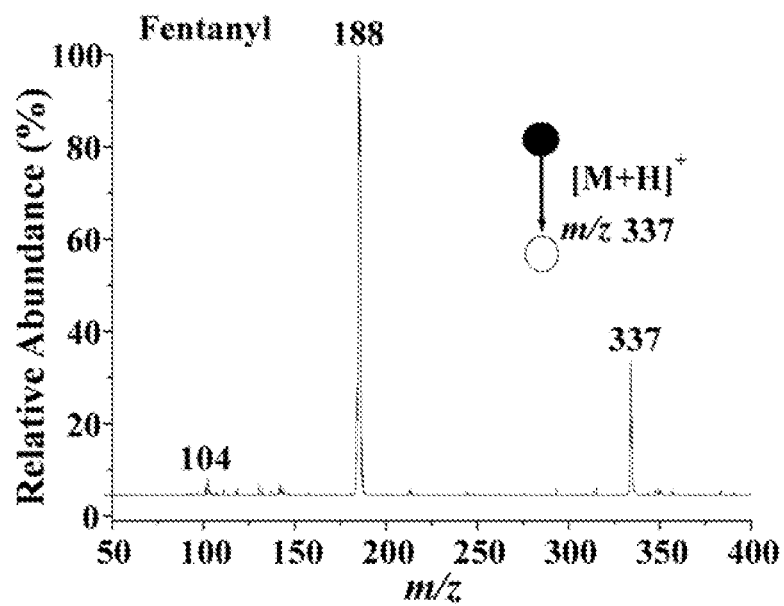
FIG. 2 is the MS/MS spectrum of fentanyl.
Figure 3:
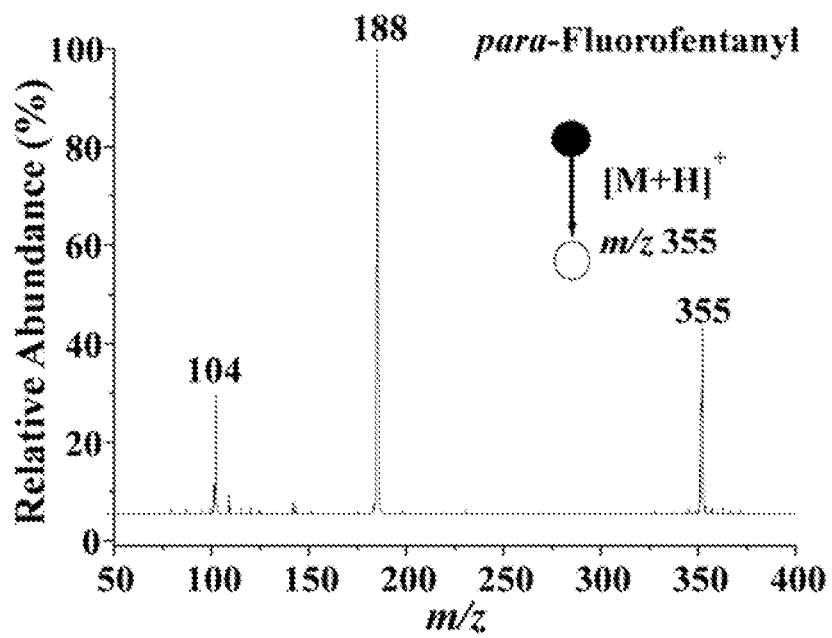
FIG. 3 is the MS/MS spectrum of para-flufentanyl.
Figure 4:
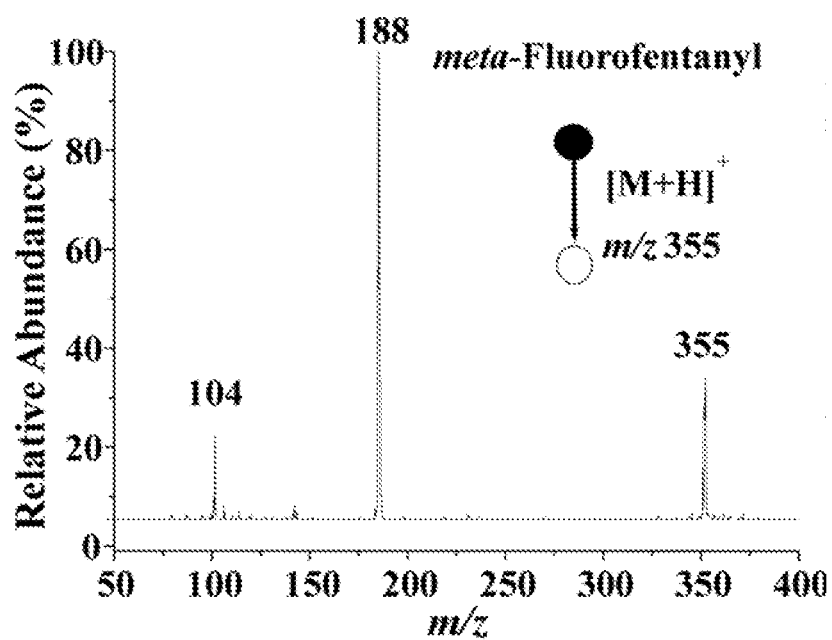
FIG. 4 is the MS/MS spectrum of meta-flufentanyl.
Figure 5:
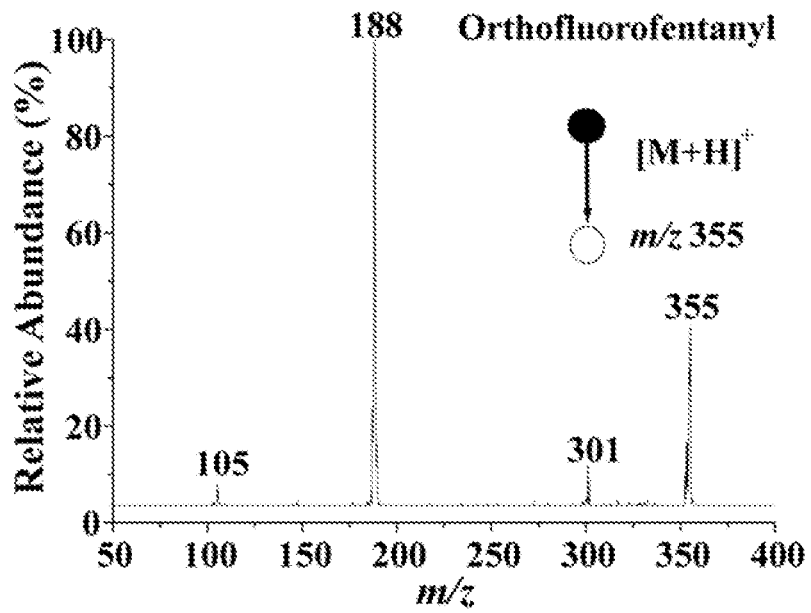
FIG. 5 is the MS/MS spectrum of ortho-flufentanyl.
Figure 6:
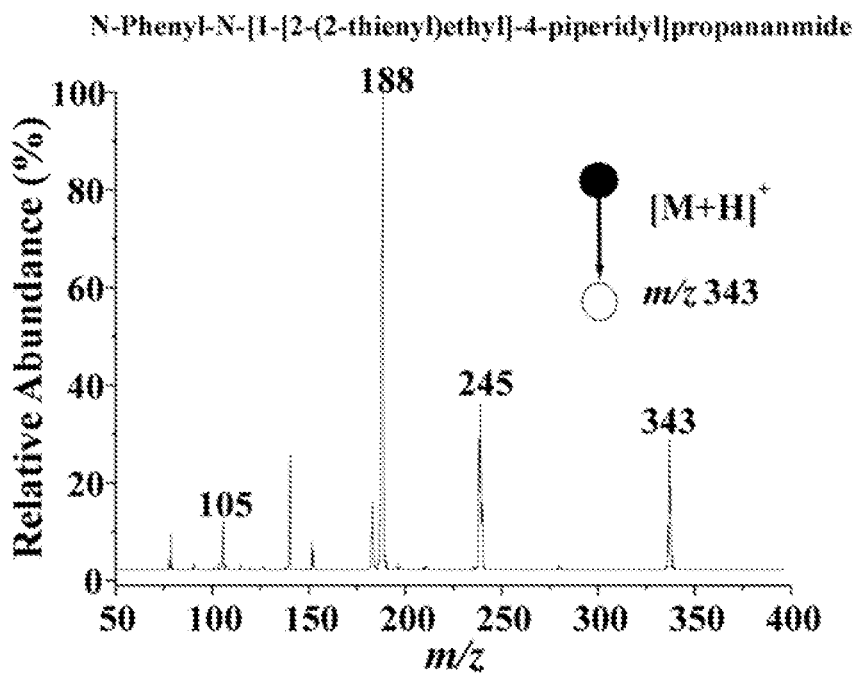
FIG. 6 is the MS/MS spectrum of N-phenyl-N-[1-[2-(2-thienyl)ethyl]-4-piperidyl]propanamide.
Figure 7:
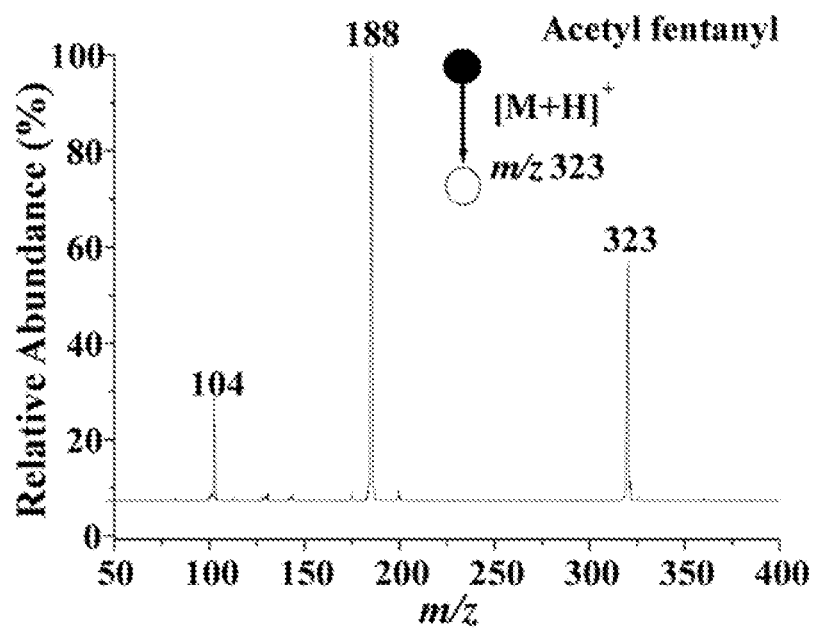
FIG. 7 is the MS/MS spectrum of acetylfentanyl.
Figure 8:
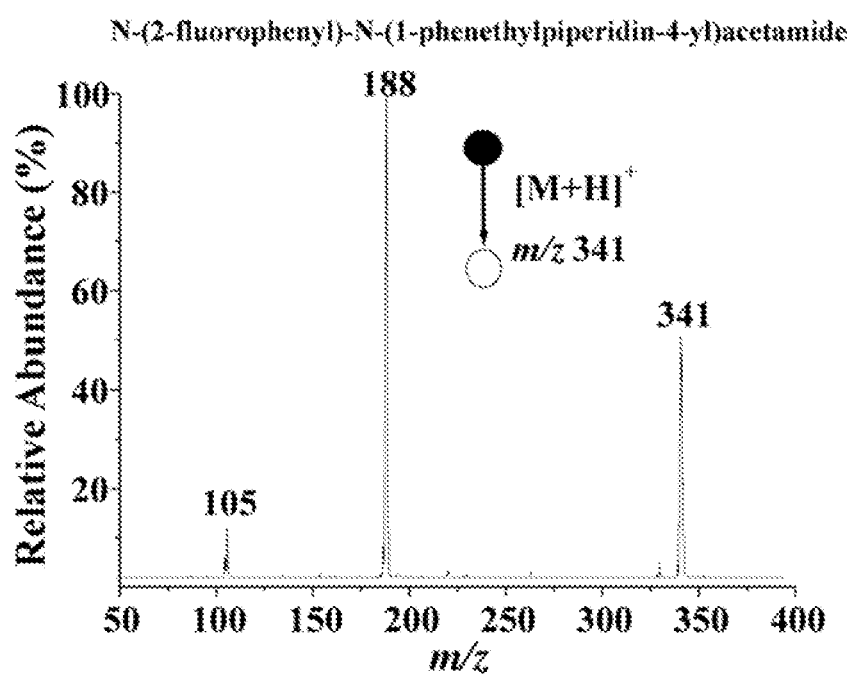
FIG. 8 is the MS/MS spectrum of N-(2-fluorophenyl)-N-(1-phenethylpiperidin-4-yl)acetamide.
Figure 9:
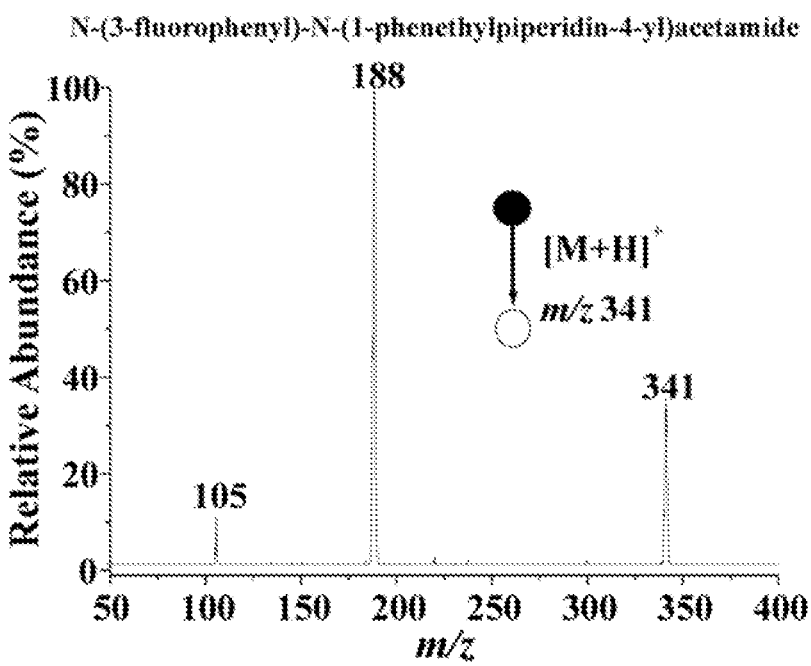
FIG. 9 is the MS/MS spectrum of N-(3-fluorophenyl)-N-(1-phenethylpiperidin-4-yl)acetamide.
Figure 10:
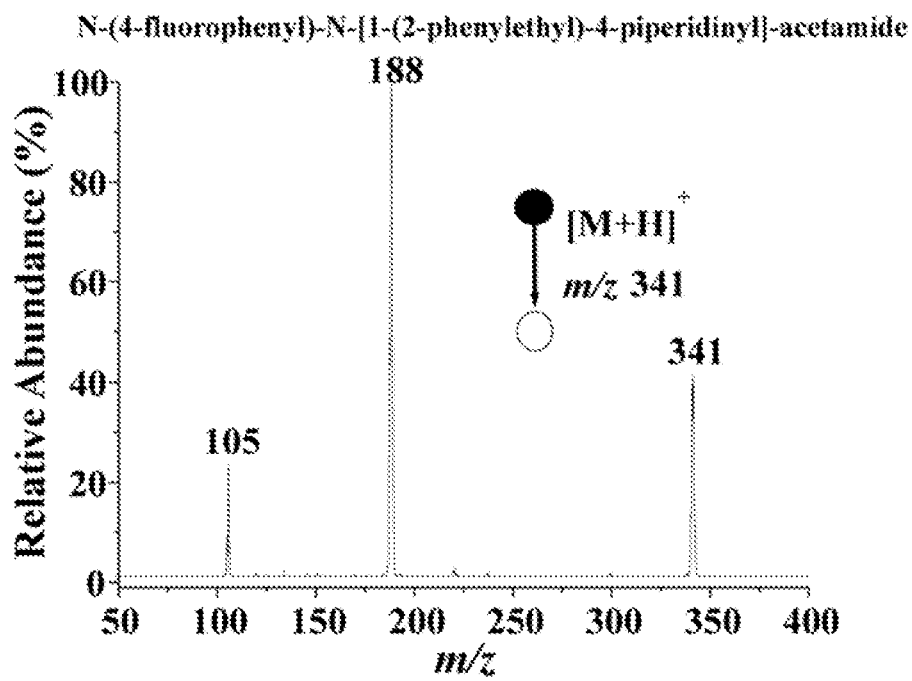
FIG. 10 is the MS/MS spectrum of N-(4-fluorophenyl)-N-[1-(2-phenylethyl)-4-piperidinyl]-acetamide.
Figure 11:
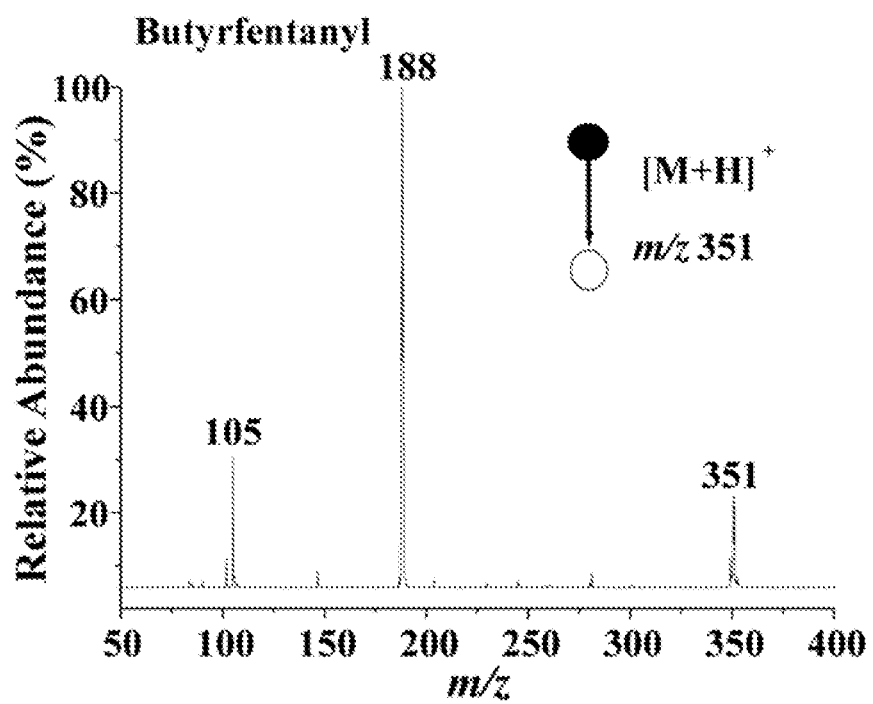
FIG. 11 is the MS/MS spectrum of butyrfentanyl.
Figure 12:
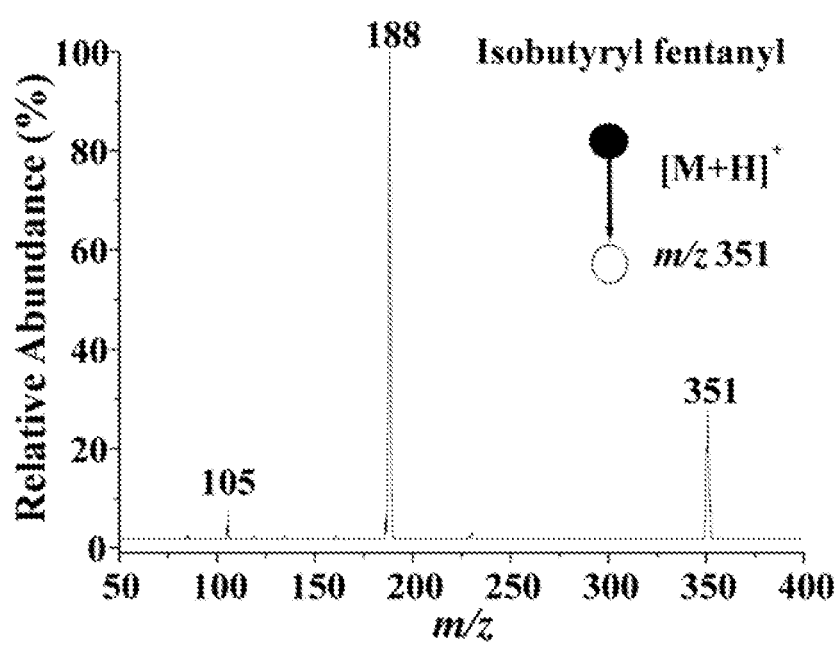
FIG. 12 is the MS/MS spectrum of isobutyryl fentanyl.
Figure 13:
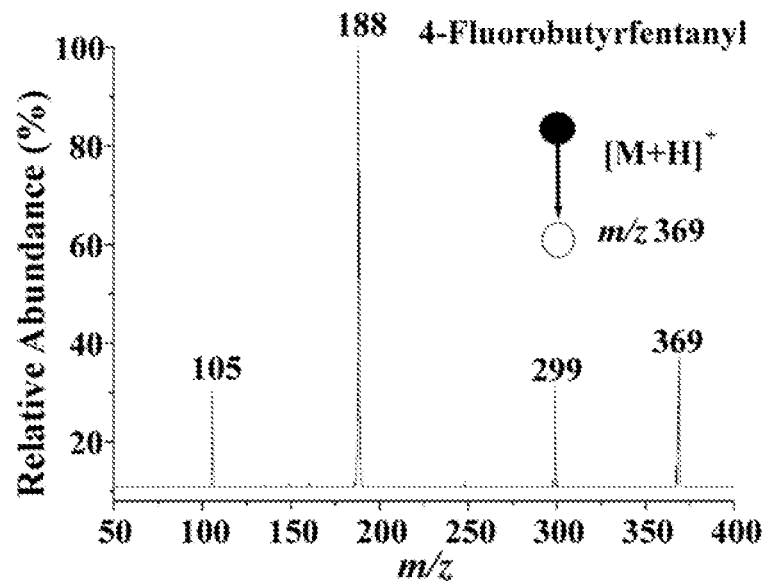
FIG. 13 is the MS/MS spectrum of 4-fluorobutyrfentanyl.
Figure 14:
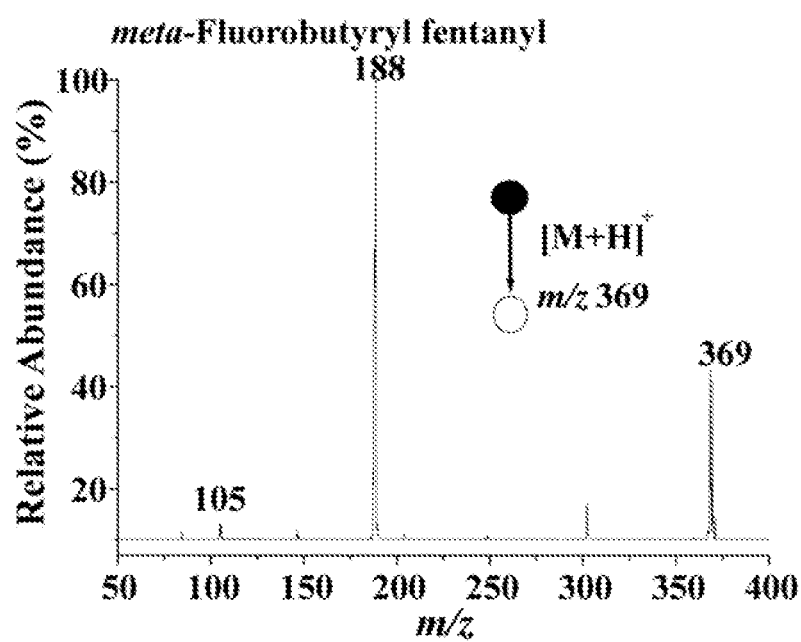
FIG. 14 is the MS/MS spectrum of meta-Fluorobutyryl fentanyl.
Figure 15:
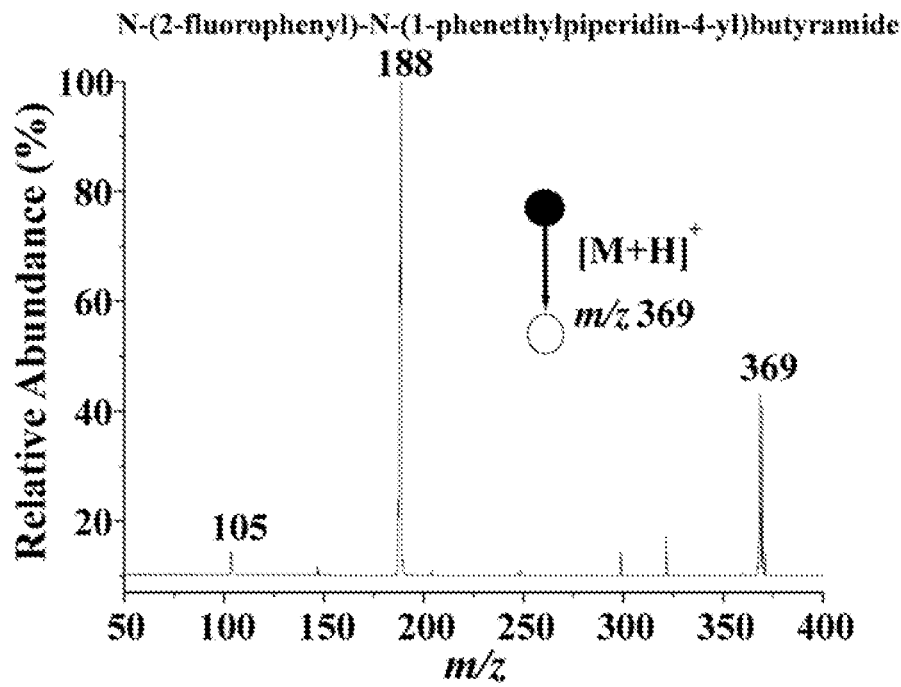
FIG. 15 is the MS/MS spectrum of N-(2-fluorophenyl)-N-(1-phenethylpiperidin-4-yl)butyramide.
Figure 16:
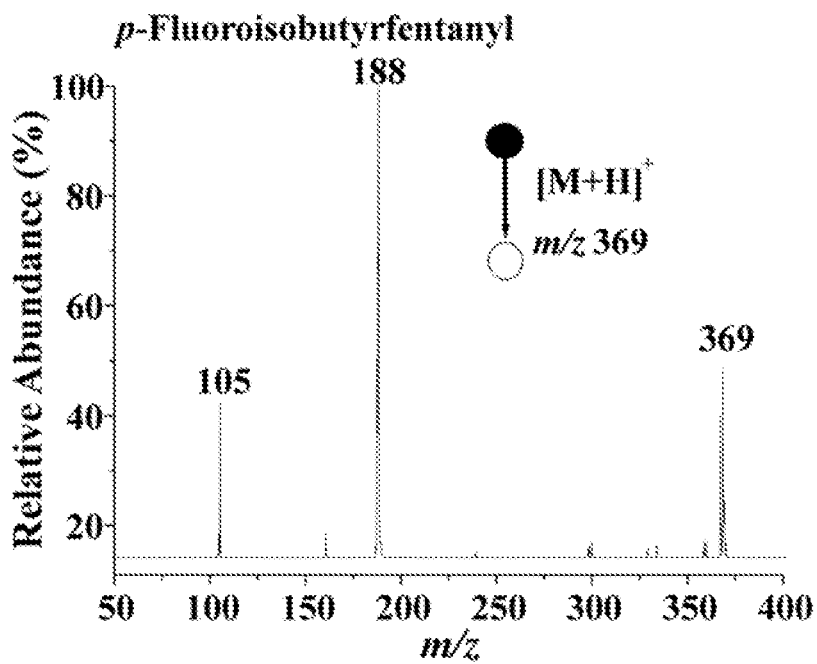
FIG. 16 is the MS/MS spectrum of para-fluoroisobutyrfentanyl.
Figure 17:
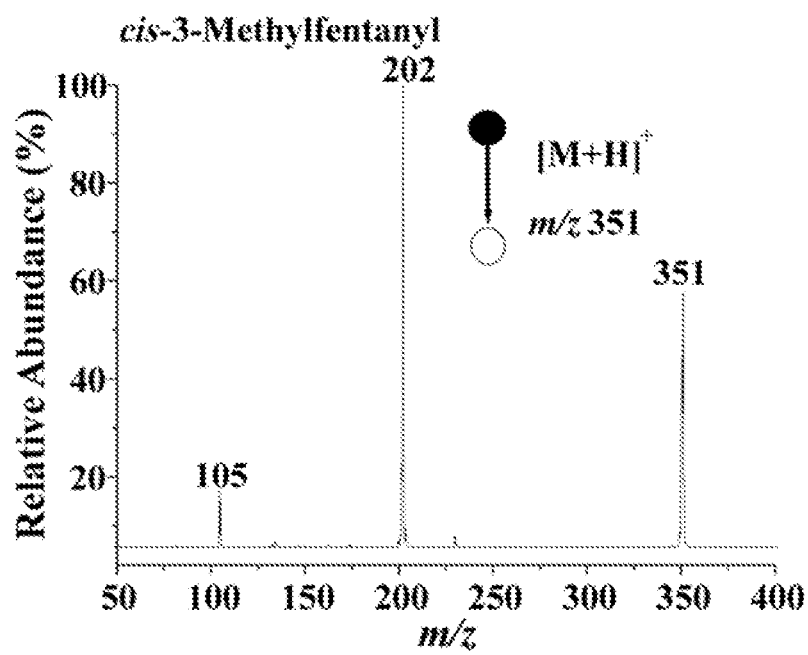
FIG. 17 is the MS/MS spectrum of cis-3-Methylfentanyl.
Figure 18:
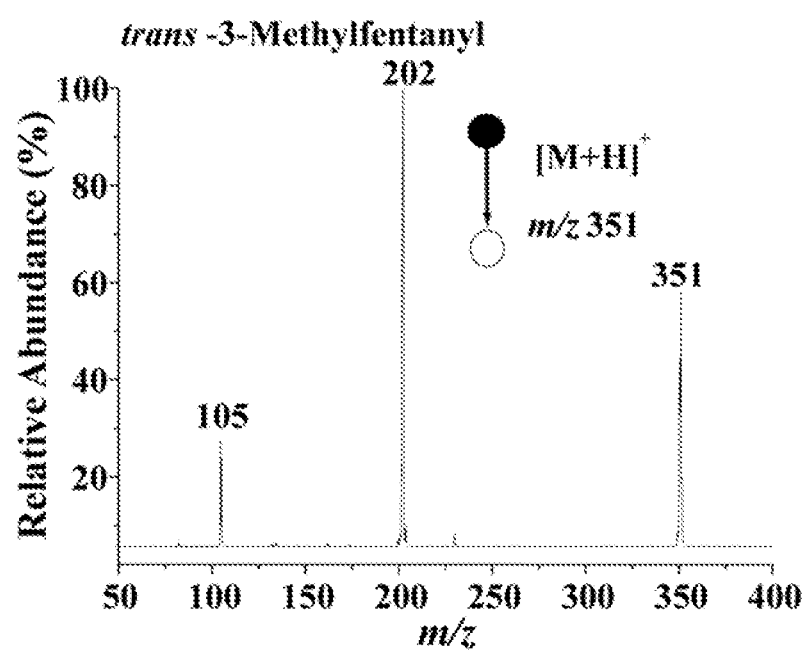
FIG. 18 is the MS/MS spectrum of trans-3-methylfentanyl.
Figure 19:
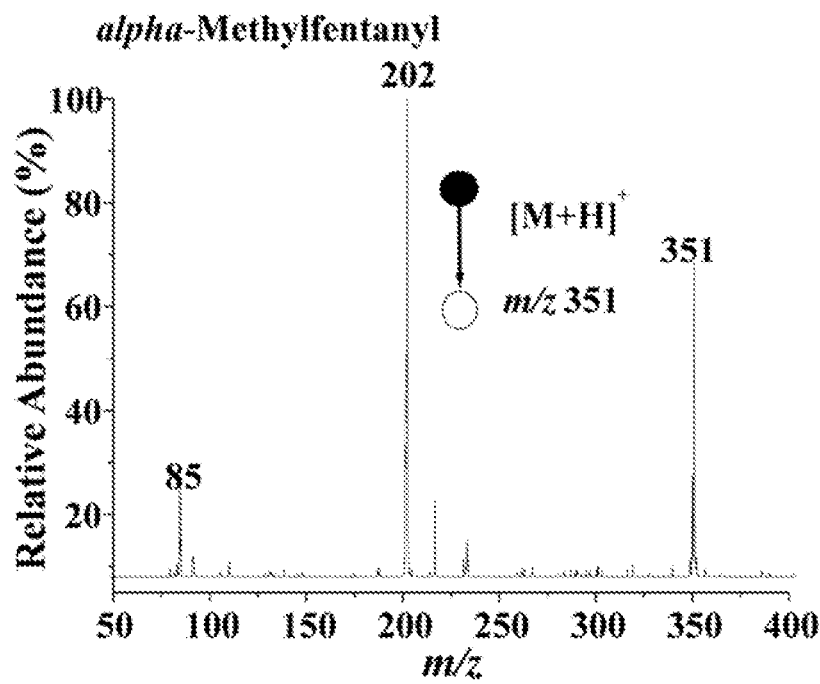
FIG. 19 is the MS/MS spectrum of alpha-methylfentanyl.
Figure 20:
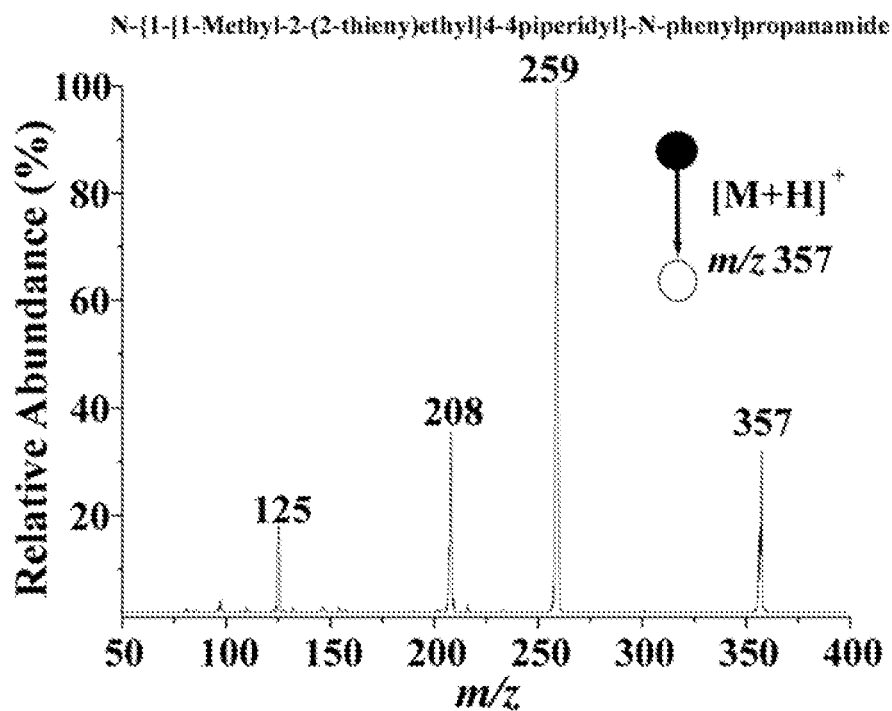
FIG. 20 is the MS/MS spectrum of N[1-[1-Methyl-2-(2-thienyl)ethyl]-4-piperidyl]-N-phenylpropanamide.
Figure 21:
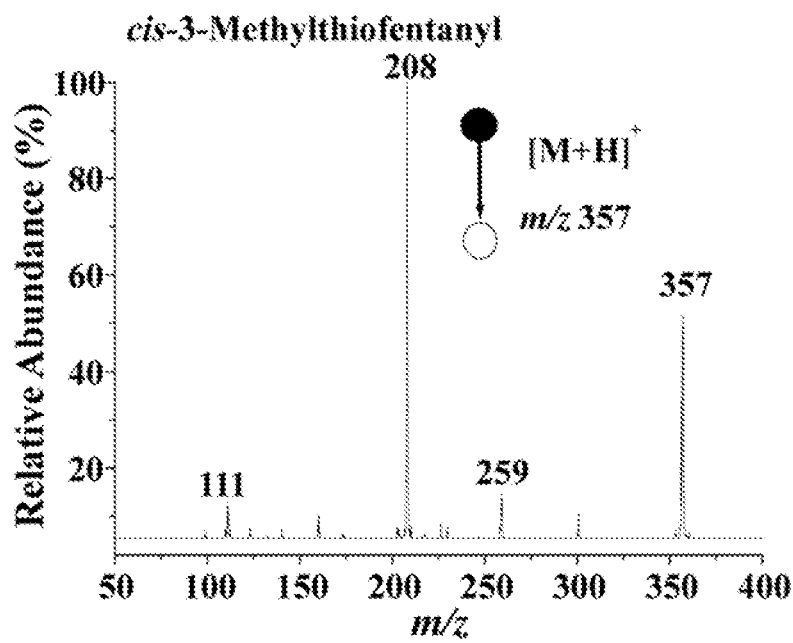
FIG. 21 is the MS/MS spectrum of cis-3-methylthiofentanyl.
Figure 22:
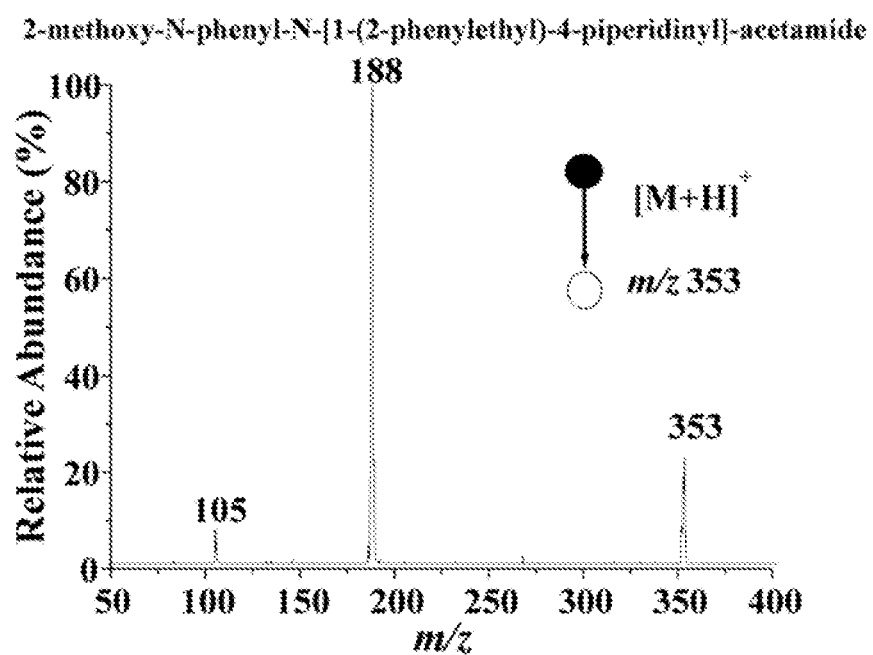
FIG. 22 is the MS/MS spectrum of 2-methoxy-N-phenyl-N[1-(2-phenylethyl)-4-piperidinyl]-acetamide.
Figure 23:
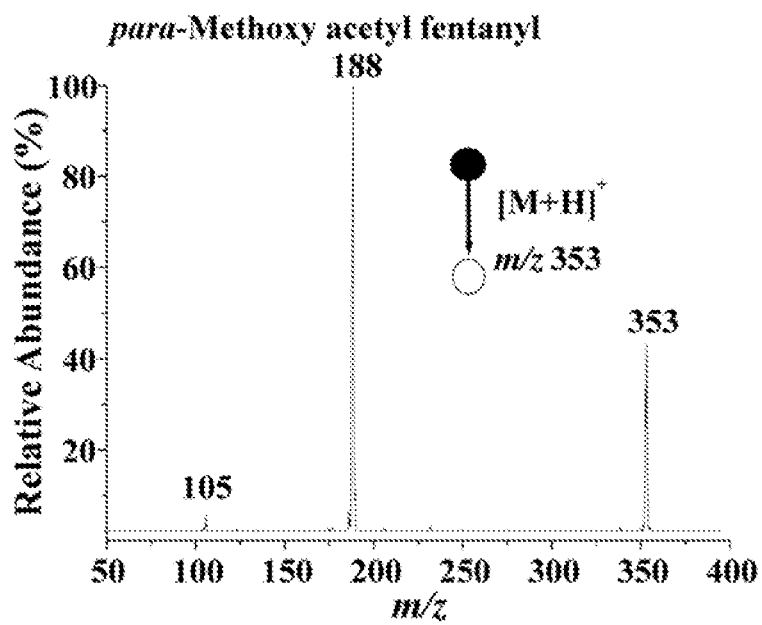
FIG. 23 is the MS/MS spectrum of para-methoxy acetyl fentanyl.
Figure 24:
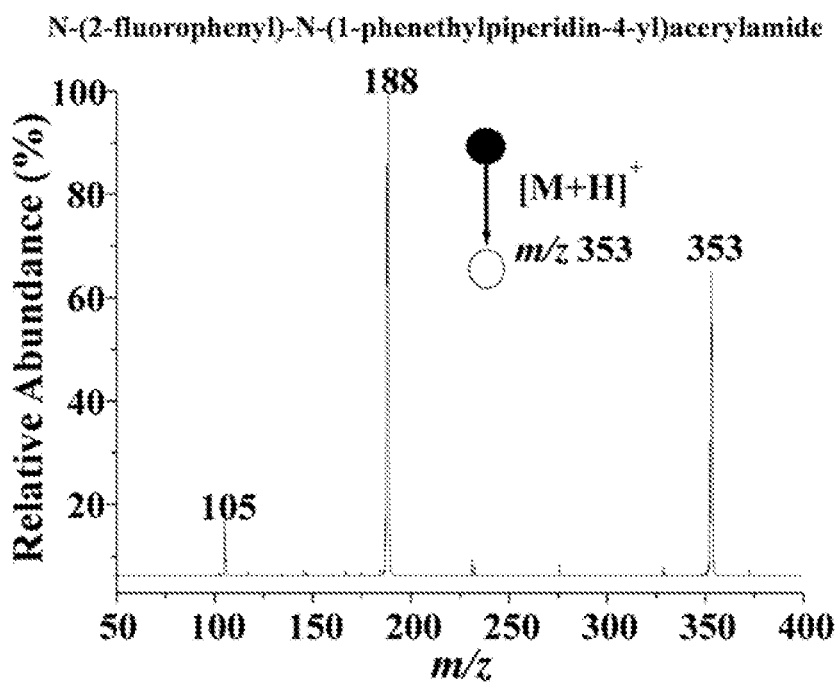
FIG. 24 is the MS/MS spectrum of N-(2-fluorophenyl)-N-(1-phenethylpiperidin-4-yl)acrylamide.
Figure 25:
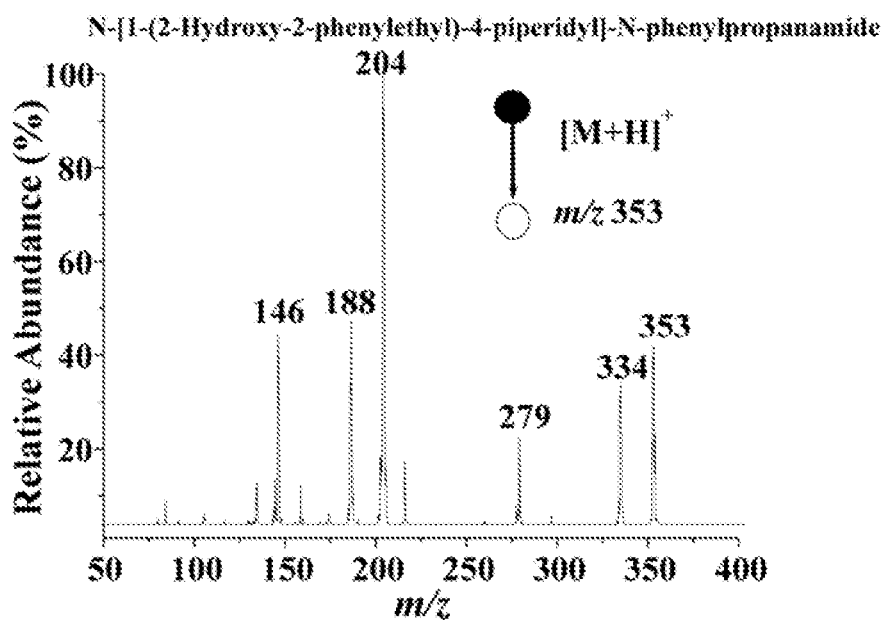
FIG. 25 is the MS/MS spectrum of N[1-(2-hydroxy-2-phenylethyl)-4-piperidyl]-N-phenylpropanamide.
Figure 26:
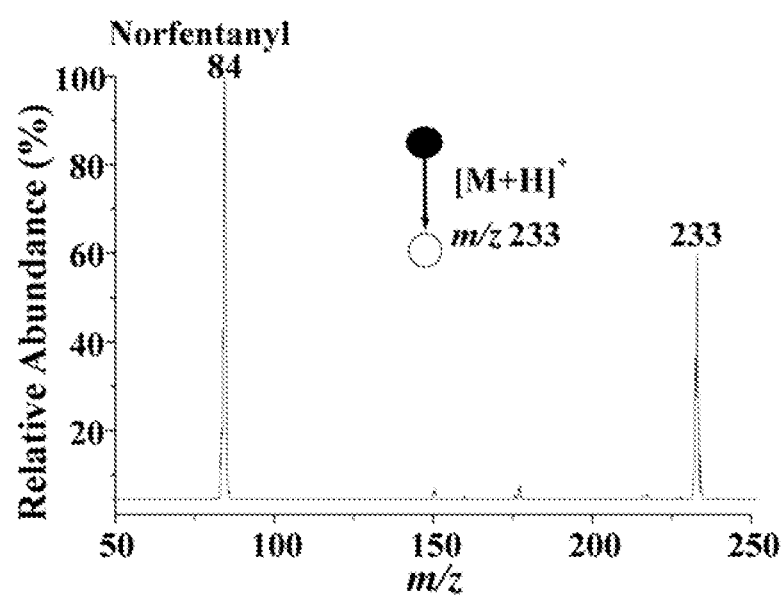
FIG. 26 is the MS/MS spectrum of norfentanyl.
Figure 27:
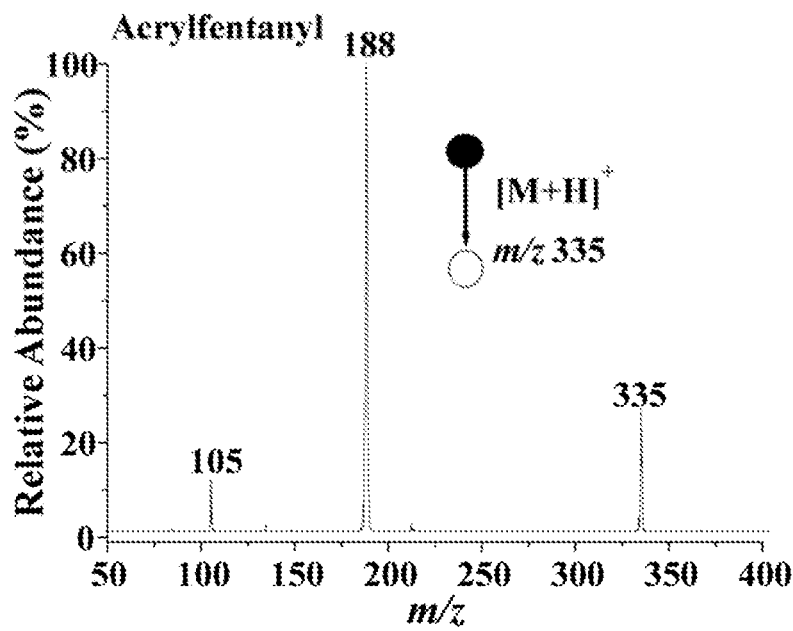
FIG. 27 is the MS/MS spectrum of acrylfentanyl.
Figure 28:
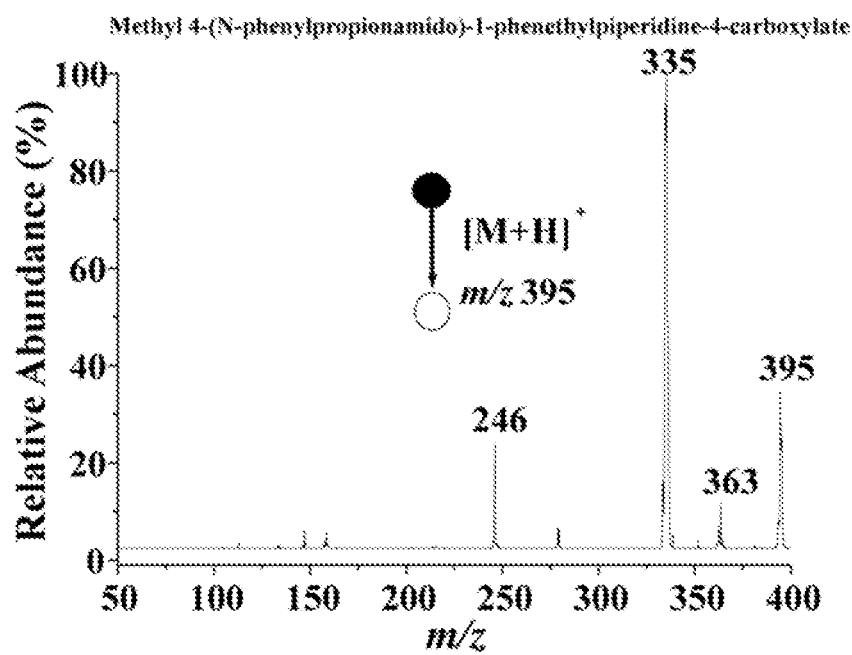
FIG. 28 is the MS/MS spectrum of methyl-4-(N-phenyl-propionamido)-1-phenethylpiperidine-4-carboxylate.
Figure 29:
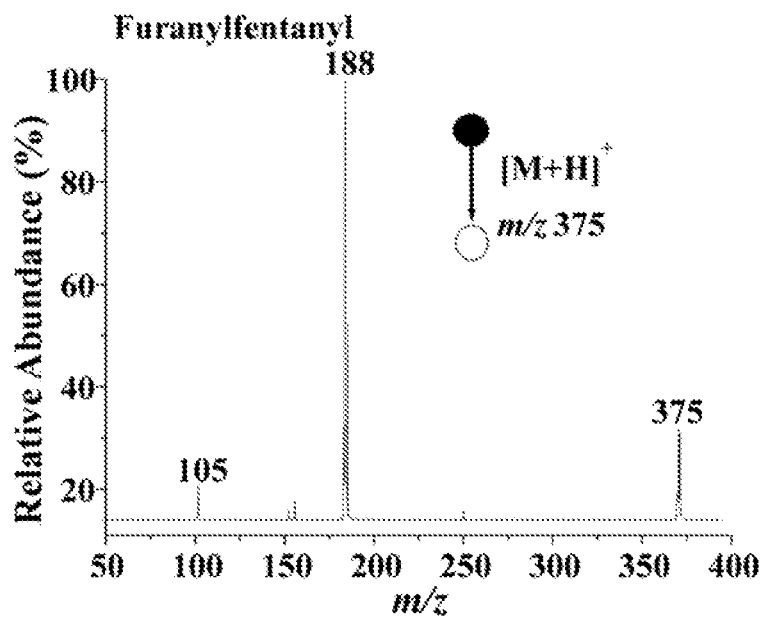
FIG. 29 is the MS/MS spectrum of furanylfentanyl.
Figure 30:
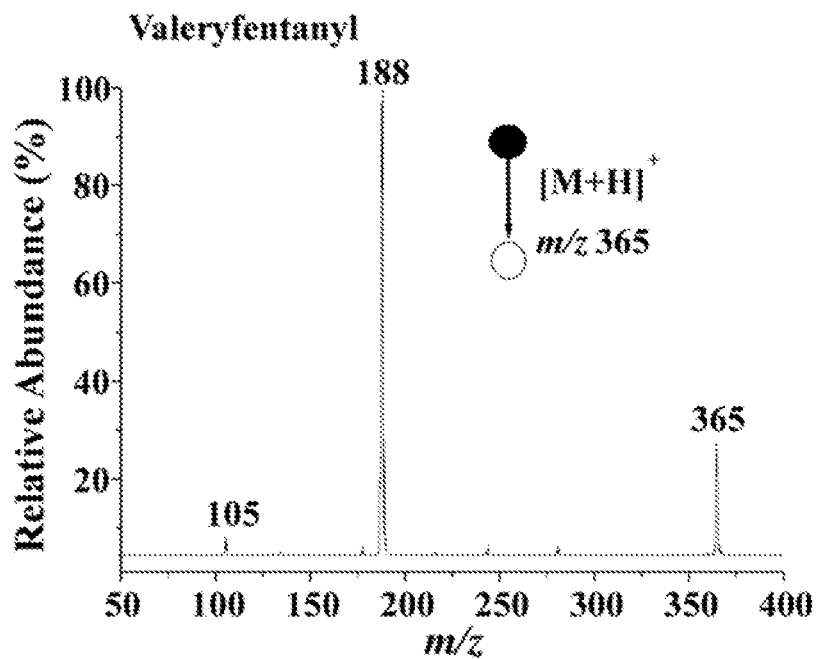
FIG. 30 is the MS/MS spectrum of valerylfentanyl.
Figure 31:
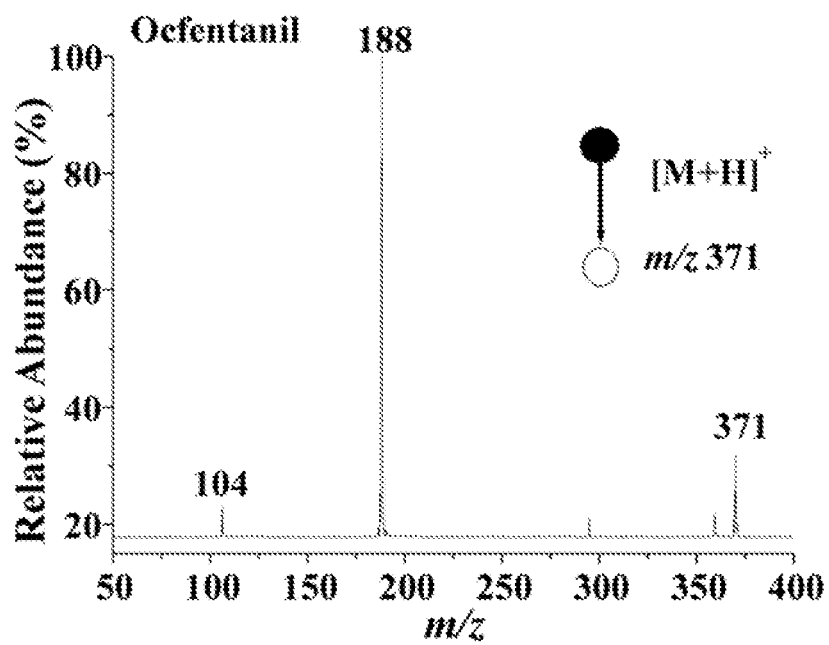
FIG. 31 is the MS/MS spectrum of ocfentanil.
Figure 32:
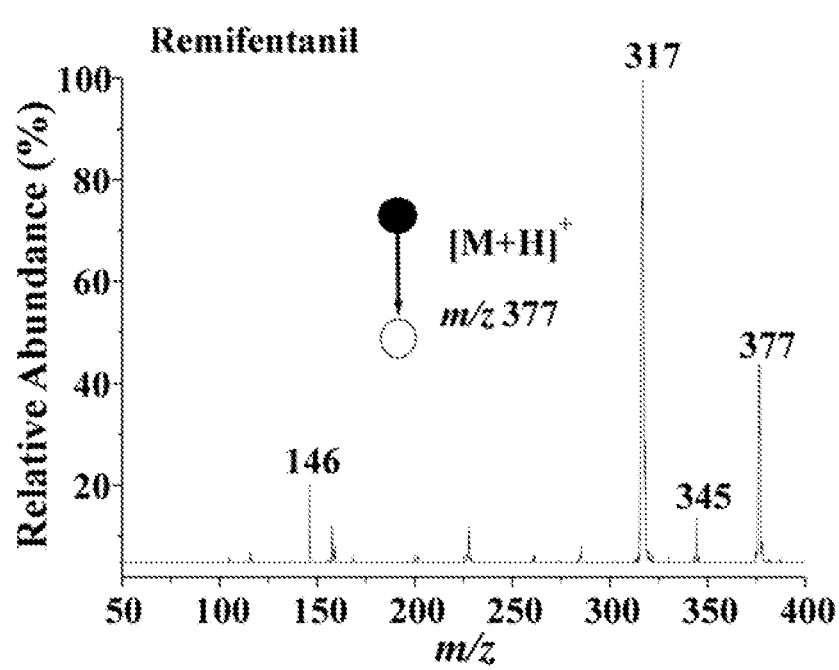
FIG. 32 is the MS/MS spectrum of remifentanil.
Figure 33:
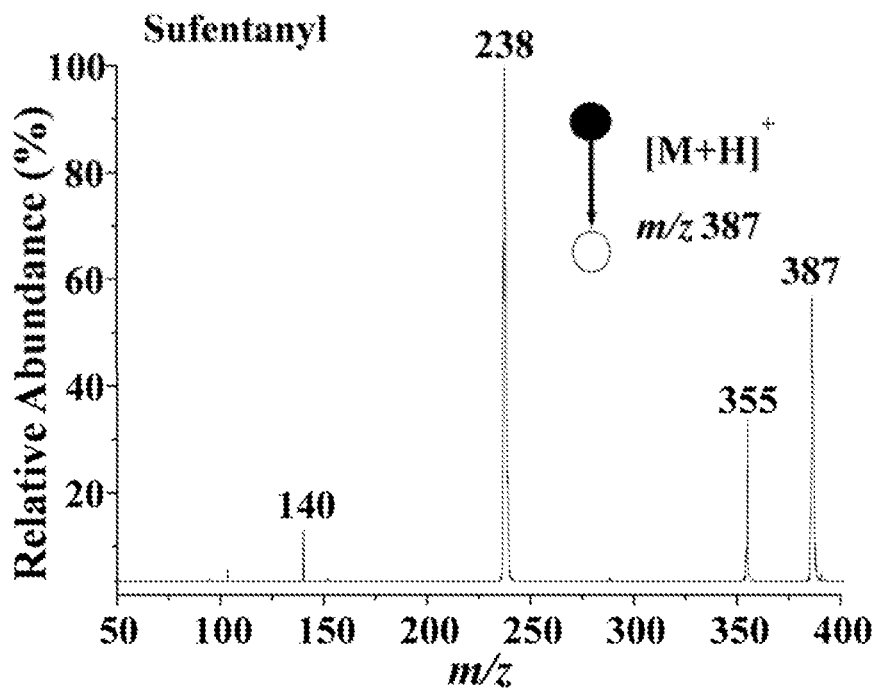
FIG. 33 is the MS/MS spectrum of sufentanyl.
Figure 34:
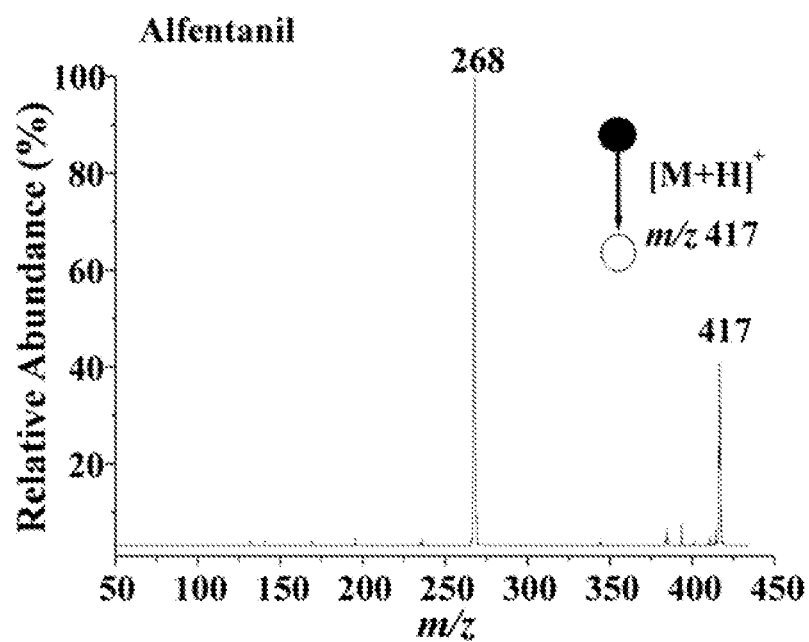
FIG. 34 is the MS/MS spectrum of alfentanil.
Figure 35:
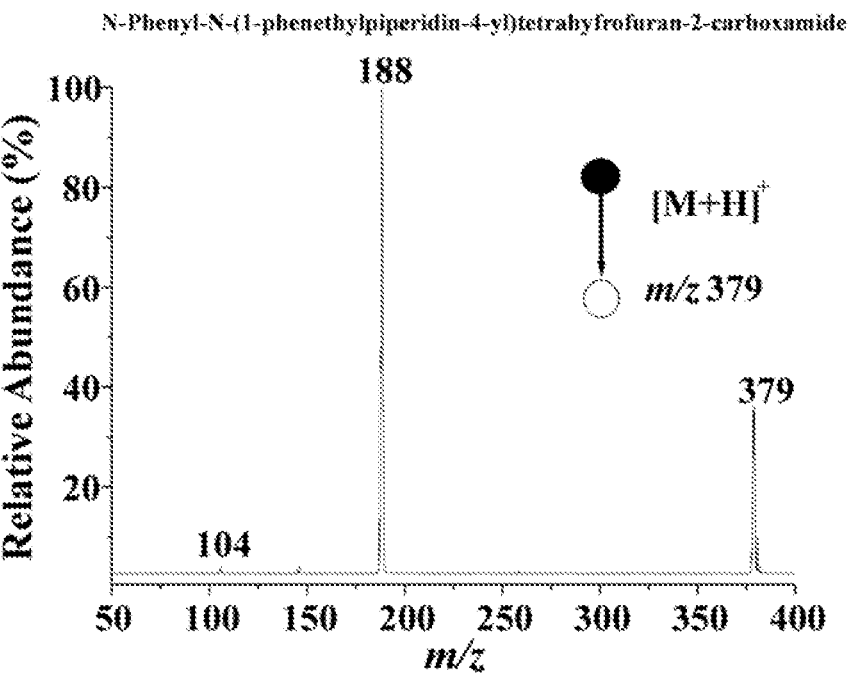
FIG. 35 is the MS/MS spectrum of N-phenyl-N-(1-phenethylpiperidin-4-yl)tetrahydrofuran-2-carboxamide.
Figure 36:
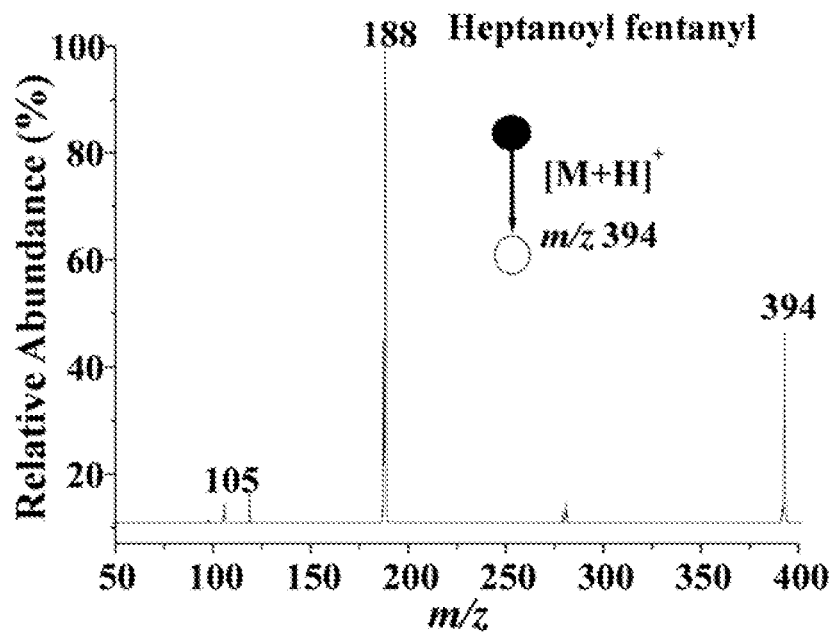
FIG. 36 is the MS/MS spectrum of heptanoyl fentanyl.
Figure 37:
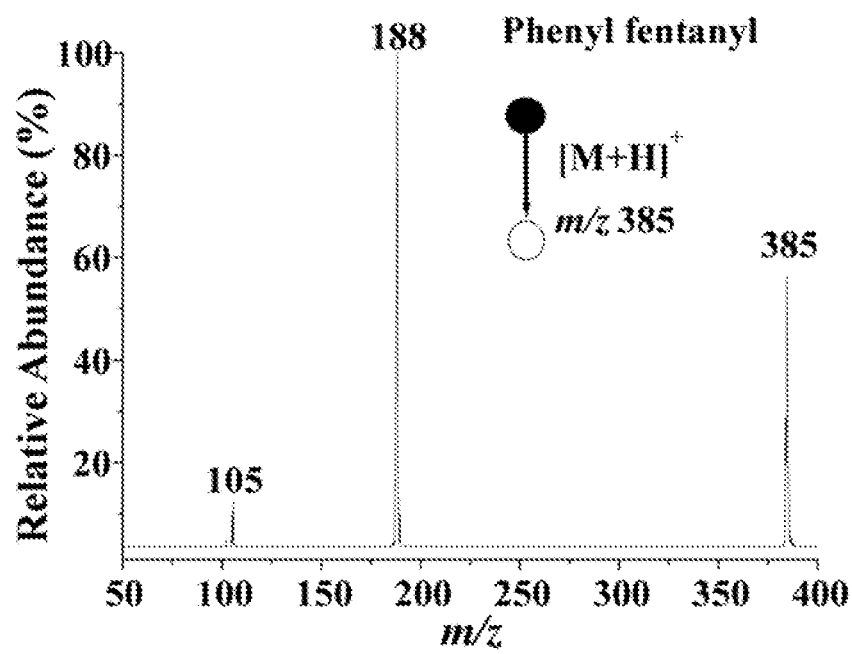
FIG. 37 is the MS/MS spectrum of phenyl fentanyl.
Figure 38:
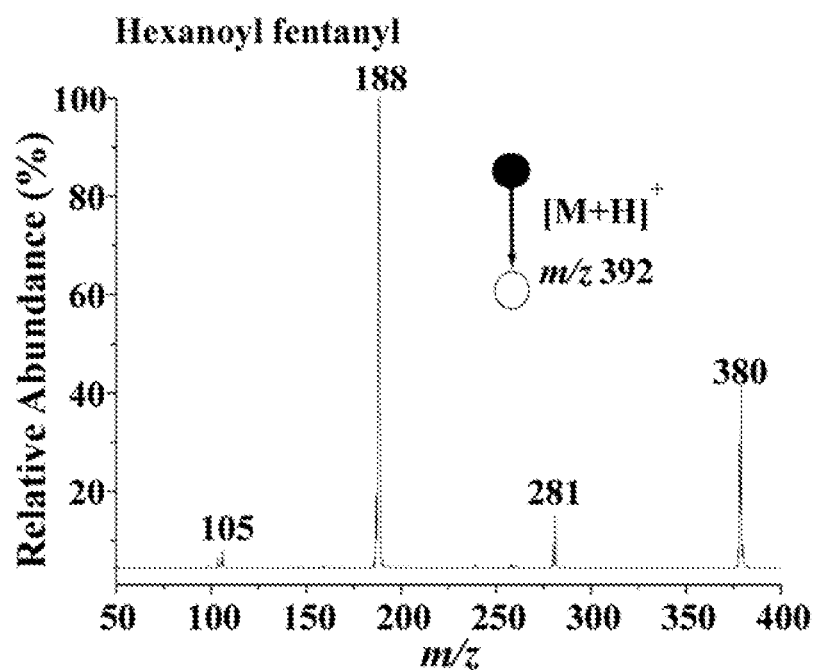
FIG. 38 is the MS/MS spectrum of hexanoyl fentanyl.
Figure 39:
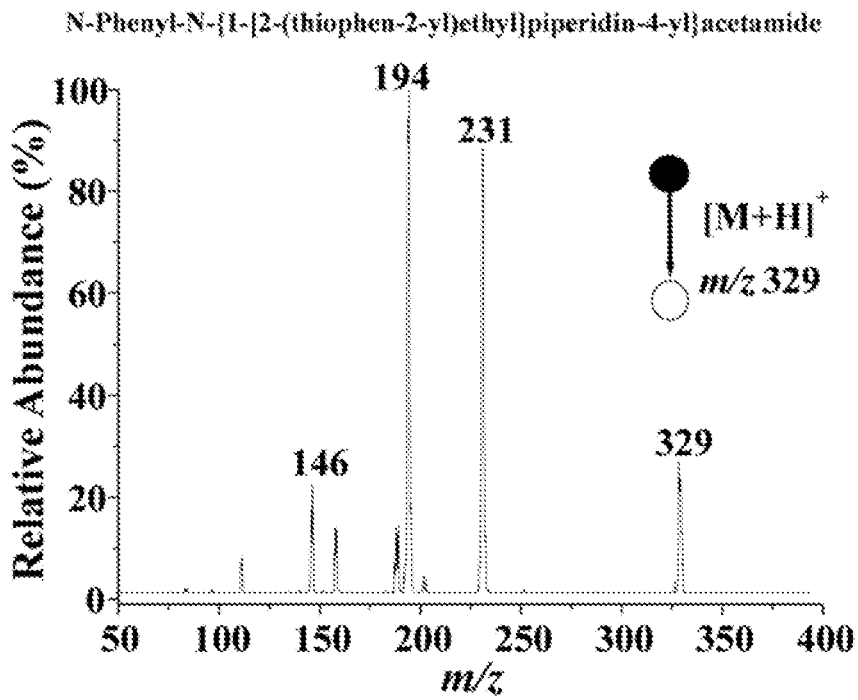
FIG. 39 is the MS/MS spectrum of N-phenyl-N-(1-(2-(thiophen-2-yl)ethyl)piperidin-4-yl)acetamide.
Figure 40:
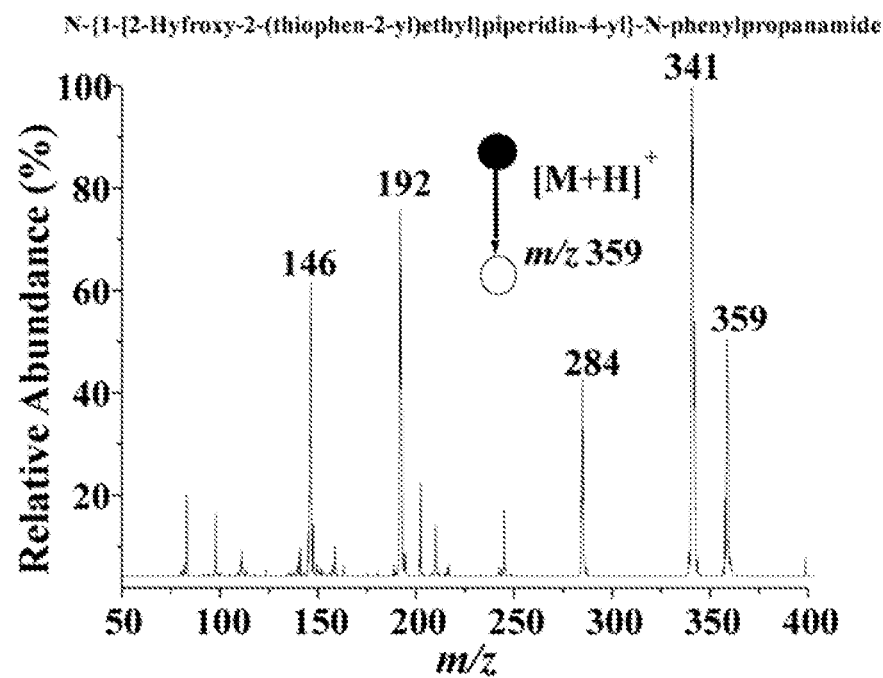
FIG. 40 is the MS/MS spectrum of N-(1-(2-hydroxy-2-(thiophen-2-ypethyl)piperidin-4-yl)-N-phenylpropanamide.
Figure 41:
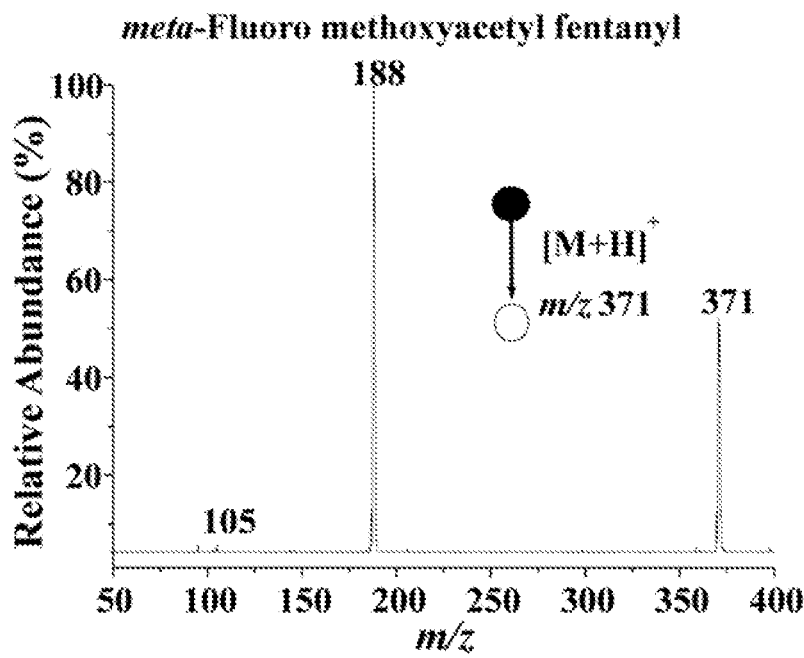
FIG. 41 is the MS/MS spectrum of meta-fluoro methoxyacetyl fentanyl.
Figure 42:
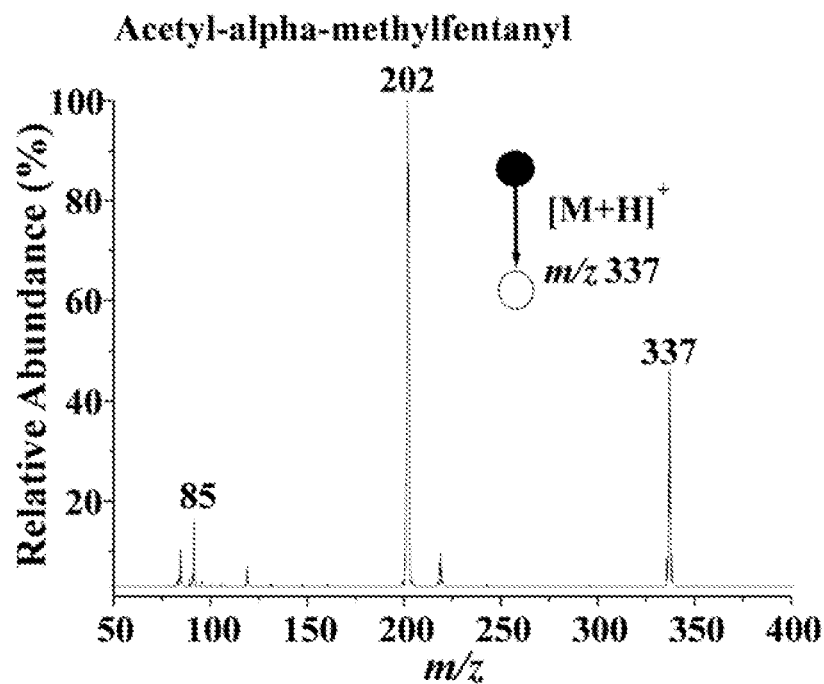
FIG. 42 is the MS/MS spectrum of acetyl-alpha-methylfentanyl.
Figure 43:
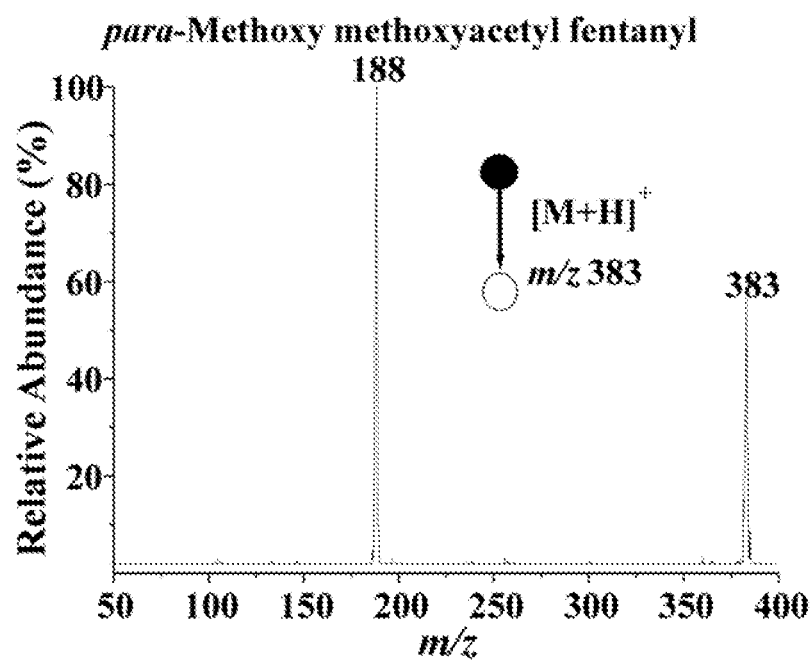
FIG. 43 is the MS/MS spectrum ofpara-methoxy methoxyacetyl fentanyl.
Figure 44:
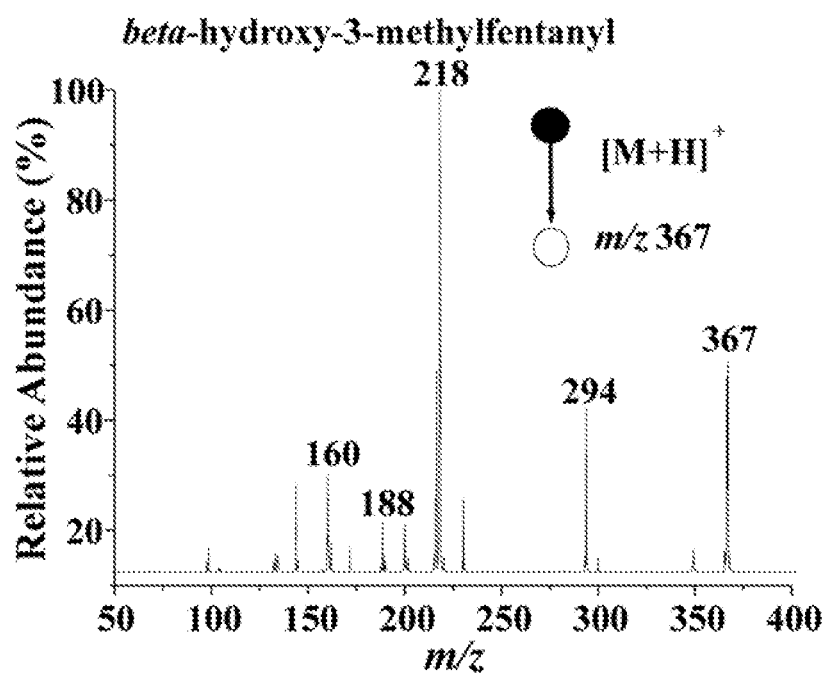
FIG. 44 is the MS/MS spectrum of beta-hydroxy-3-methylfentanyl.
Figure 45:
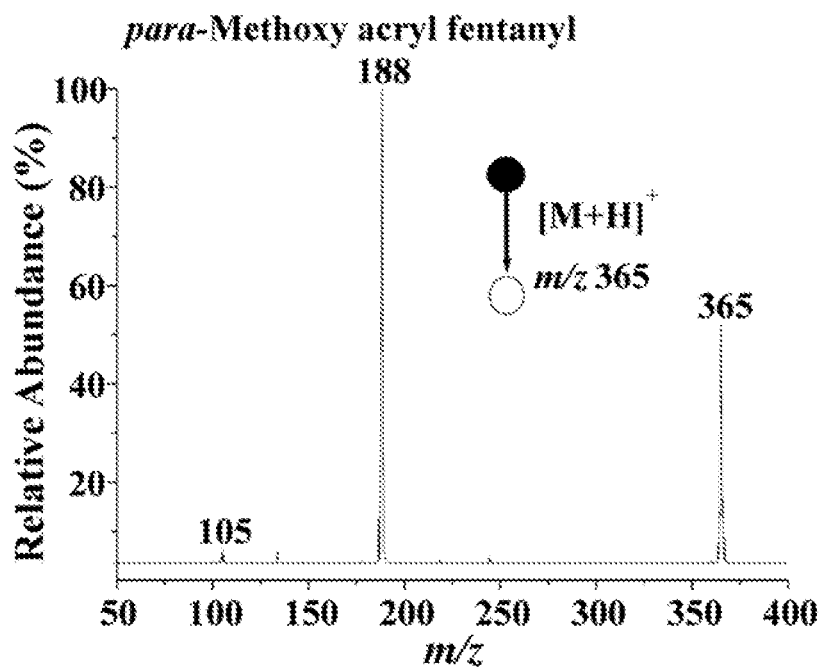
FIG. 45 is the MS/MS spectrum ofpara-methoxy acryl fentanyl.
Figure 46:
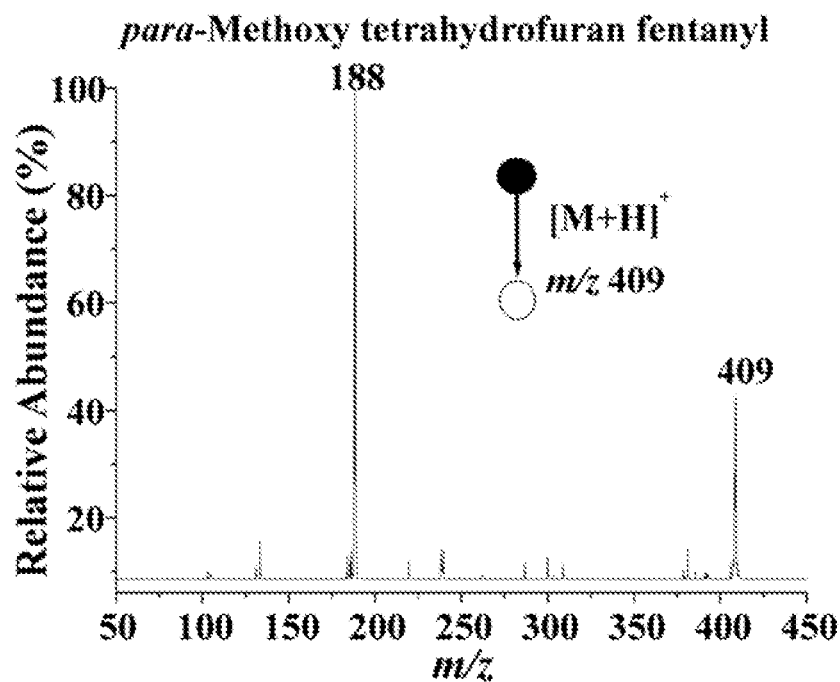
FIG. 46 is the MS/MS spectrum ofpara-methoxy tetrahydrofuran fentanyl.
Figure 47:
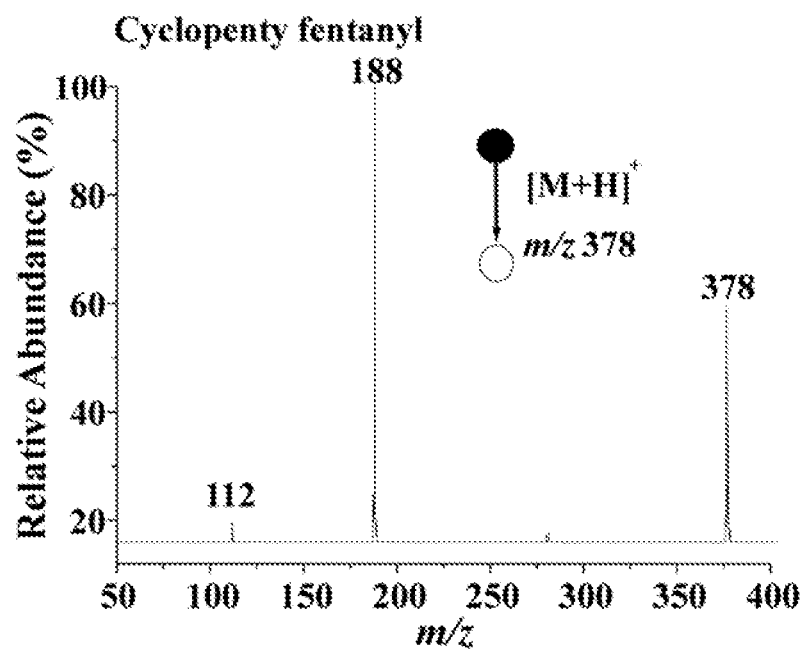
FIG. 47 is the MS/MS spectrum of cyclopentyl fentanyl.
Figure 48:
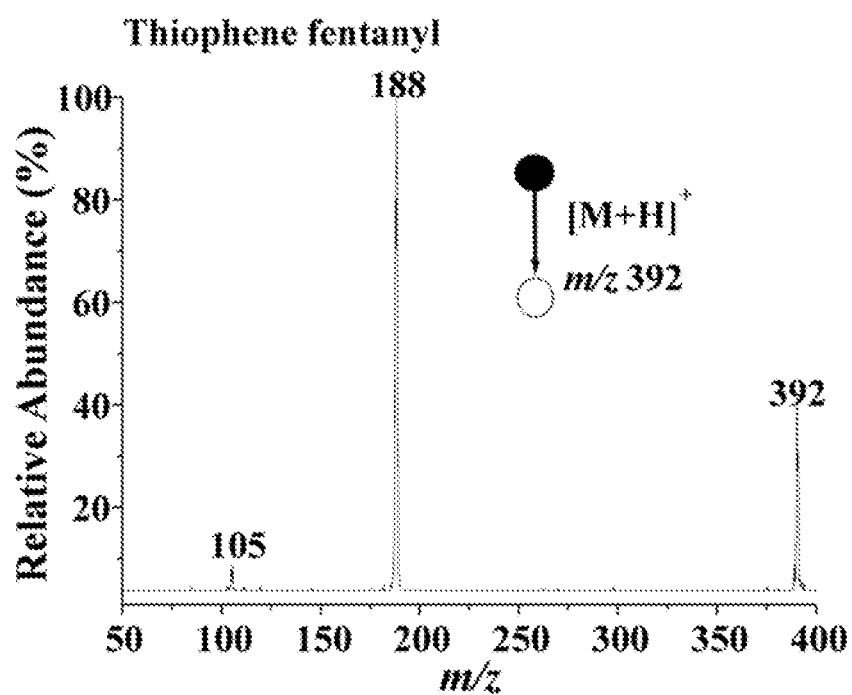
FIG. 48 is the MS/MS spectrum of thiophene fentanyl.
Figure 49:
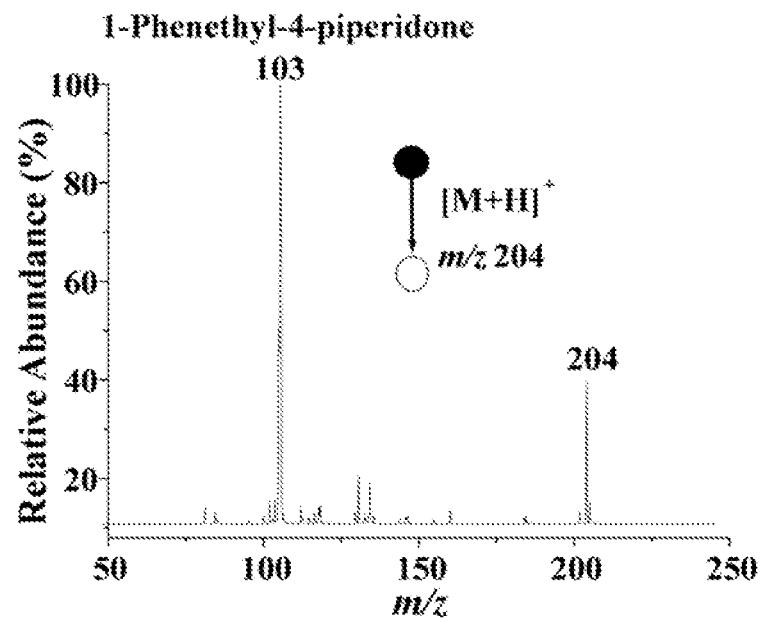
FIG. 49 is the MS/MS spectrum of 1-phenethyl-4-piperidone.
Figure 50:
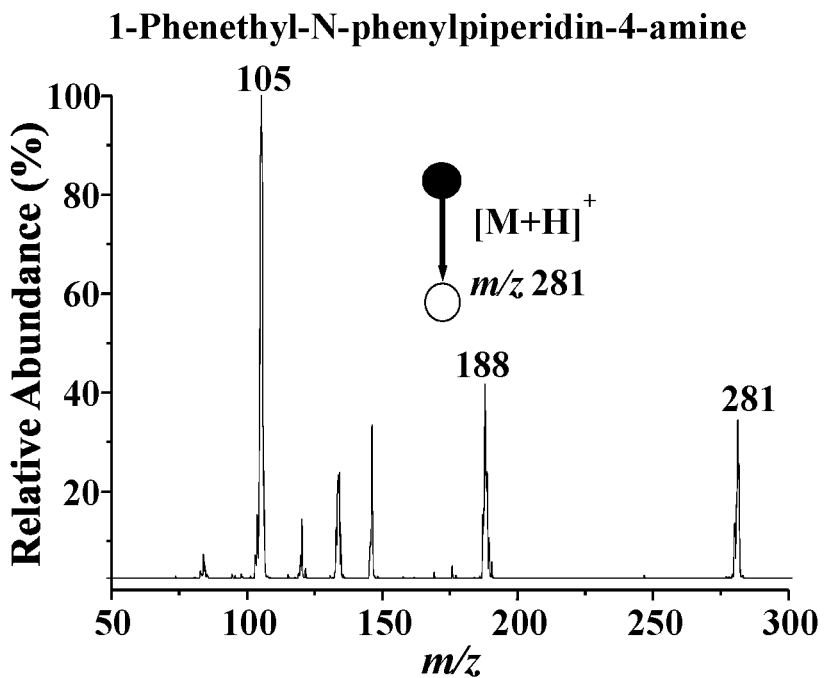
FIG. 50 is the MS/MS spectrum of 1-phenethyl-N-phenylpiperidin-4-amine.

The parameters of the miniature mass spectrometer were set according to the data in Table 1, and the crystalline mixture on the tip of the triangular paper substrate was placed in close proximity to the inlet of the miniature mass spectrometer for 3 seconds for analysis and detection. The mass spectrum is shown in FIG. 2.

The invention optimizes the selection of the spotting plates. Under the same experimental conditions, a filter paper, a triangular paper substrate, a glass slide, an aluminum foil, a centrifuge tube cap or a cotton swab were investigated as different spotting plates. The signal intensities of the miniature mass spectrometer were compared. The experiments were conducted in 6 replicates for each kind of spotting plates, and the average results were compared. The data were normalized and compared, and the results were shown in FIG. 1. It can be seen from FIG. 1 that when the triangular paper substrate was selected as the spotting plate, the mass spectrometric signal was the most intensive, so the triangular paper substrate was selected as the optimal spotting plate.

The foregoing embodiments are merely illustrative of preferred embodiments of the present invention and are not intended to limit the scope of the present invention. Various variations and modifications made to the technical solutions of the present invention by those skilled in the art without departing from the spirit of the present invention are embraced in the protection scope of the present invention as defined by the appended claims.

What is claimed is:

1. A method for rapid on-site detection of fentanyl analogs using a miniature mass spectrometer, comprising the following steps:
   (1) selecting a spotting plate;
   (2) loading a sample: depositing the sample and 3-nitrobenzonitrile solution in acetonitrile on the spotting plate to form a crystalline mixture;
   (3) carrying out analysis and detection: setting the parameters of the miniature mass spectrometer, placing the crystalline mixture on the spotting plate in close proximity to the inlet of the miniature mass spectrometer, and facilitating the ionization of the crystalline mixture for the analysis and detection of fentanyl analogs;
   wherein the sample comprises powder, blood, and sweat; there are 49 kinds of fentanyl analogs, and the analysis parameters of the miniature mass spectrometer and LODs in step (3) are as shown in Table 1;

TABLE 1

The analysis parameters of the miniature mass spectrometer and limits of detection(LODs) for the 49 fentanyl analogs

| Fentanyl analogs | Ionization mode | m/z | RF/kHz | AC/kHz | CID-AC/kHz | CID-AC/Vpp | LOD/(μg/kg) |
|---|---|---|---|---|---|---|---|
| fentanyl | positive | 337 | 150-800 | 5-46 | 47 | 220 | 20 |
| para-flufentanyl | positive | 355 | 150-880 | 5-42 | 43 | 220 | 20 |
| meta-flufentanyl | positive | 355 | 150-860 | 5-43 | 44 | 220 | 20 |
| ortho-flufentanyl | positive | 355 | 150-860 | 5-42 | 43 | 210 | 20 |
| N-phenyl-N-[1-[2-(2-thienyl)ethyl]-4-piperidyl]propanamide | positive | 343 | 150-840 | 5-44 | 45 | 220 | 50 |
| acetylfentanyl | positive | 323 | 150-780 | 5-45 | 46 | 210 | 50 |
| N-(2-fluorophenyl)-N-(1-phenethylpiperidin-4-yl)acetamide | positive | 341 | 150-820 | 5-44 | 45 | 215 | 20 |
| N-(3-fluorophenyl)-N-(1-phenethylpiperidin-4-yl)acetamide | positive | 341 | 150-820 | 5-44 | 45 | 220 | 20 |
| N-(4-fluorophenyl)-N-[1-(2-phenylethyl)-4-piperidinyl]-acetamide | positive | 341 | 150-820 | 5-44 | 45 | 220 | 20 |
| butyrfentanyl | positive | 351 | 150-830 | 5-43 | 44 | 235 | 50 |
| isobutyryl fentanyl | positive | 351 | 150-840 | 5-42 | 43 | 222 | 50 |
| 4-fluorobutyrfentanyl | positive | 369 | 150-900 | 5-40 | 41 | 225 | 50 |
| meta-fluorobutyryl fentanyl | positive | 369 | 150-880 | 5-40 | 41 | 220 | 50 |
| N-(2-fluorophenyl)-N-(1-phenethylpiperidin-4-yl)butyramide | positive | 369 | 150-880 | 5-40 | 41 | 220 | 50 |
| para-fluoroisobutyrfentanyl | positive | 369 | 150-880 | 5-40 | 41 | 220 | 50 |
| cis-3-methylfentanyl | positive | 351 | 150-850 | 5-43 | 44 | 223 | 50 |
| trans-3-methylfentanyl | positive | 351 | 150-850 | 5-43 | 44 | 221 | 50 |
| alpha-methylfentanyl | positive | 351 | 150-850 | 5-43 | 44 | 220 | 50 |
| N-[1-[1-methyl-2-(2-thienyl)ethyl]-4-piperidyl]-N-phenylpropanamide | positive | 357 | 150-870 | 5-42 | 43 | 217 | 100 |
| cis-3-methylthiofentanyl | positive | 357 | 150-880 | 5-42 | 43 | 215 | 100 |
| 2-methoxy-N-phenyl-N-[1-(2-phenylethyl)-4-piperidinyl]-acetamide | positive | 353 | 150-840 | 5-43 | 44 | 210 | 20 |
| para-methoxy acetyl fentanyl | positive | 353 | 150-840 | 5-42 | 43 | 220 | 20 |
| N-(2-fluorophenyl)-N-(1-phenethylpiperidin-4-yl)acrylamide | positive | 353 | 150-820 | 5-43 | 44 | 215 | 20 |
| N-[1-(2-hydroxy-2-phenylethyl)-4-piperidyl]-N-phenylpropanamide | positive | 353 | 150-840 | 5-42 | 43 | 220 | 200 |
| norfentanyl | positive | 232 | 150-600 | 5-67 | 68 | 180 | 50 |
| acrylfentanyl | positive | 335 | 150-820 | 5-44 | 45 | 220 | 50 |

TABLE 1-continued

The analysis parameters of the miniature mass spectrometer and limits of detection(LODs) for the 49 fentanyl analogs

| Fentanyl analogs | Ionization mode | m/z | RF/kHz | AC/kHz | CID-AC/kHz | CID-AC/Vpp | LOD/(μg/kg) |
|---|---|---|---|---|---|---|---|
| methyl-4-(N-phenylpropionamido)-1-phenethylpiperidine-4-carboxylate | positive | 395 | 150-930 | 5-36 | 37 | 200 | 100 |
| furanylfentanyl | positive | 375 | 150-920 | 5-40 | 41 | 205 | 50 |
| valerylfentanyl | positive | 365 | 150-900 | 5-40 | 41 | 225 | 50 |
| ocfentanil | positive | 371 | 150-880 | 5-40 | 41 | 215 | 50 |
| remifentanil | positive | 377 | 150-940 | 5-39 | 40 | 180 | 200 |
| sufentanyl | positive | 387 | 150-950 | 5-37 | 38 | 190 | 100 |
| alfentanil | positive | 417 | 150-1000 | 5-34 | 35 | 200 | 200 |
| N-phenyl-N-(1-phenethylpiperidin-4-yl)tetrahydrofuran-2-carboxamide | positive | 379 | 150-940 | 5-38 | 39 | 205 | 50 |
| heptanoyl fentanyl | positive | 394 | 150-920 | 5-36 | 37 | 225 | 50 |
| phenyl fentanyl | positive | 385 | 150-950 | 5-38 | 39 | 210 | 20 |
| hexanoyl fentanyl | positive | 380 | 150-940 | 5-38 | 39 | 230 | 50 |
| N-phenyl-N-(1-(2-(thiophen-2-yl)ethyl)piperidin-4-yl)acetamide | positive | 329 | 150-800 | 5-45 | 46 | 215 | 100 |
| N-(1-(2-hydroxy-2-(thiophen-2-yl)ethyl)piperidin-4-yl)-N-phenylpropanamide | positive | 359 | 150-890 | 5-41 | 42 | 213 | 200 |
| meta-fluoro methoxyacetyl fentanyl | positive | 371 | 150-890 | 5-40 | 41 | 200 | 50 |
| acetyl-alpha-methylfentanyl | positive | 337 | 150-800 | 5-44 | 45 | 226 | 20 |
| para-methoxy methoxyacetyl fentanyl | positive | 383 | 150-910 | 5-38 | 39 | 210 | 50 |
| beta-hydroxy-3-methylfentanyl | positive | 367 | 150-900 | 5-40 | 41 | 225 | 50 |
| para-methoxy acryl fentanyl | positive | 365 | 150-900 | 5-40 | 41 | 220 | 50 |
| para-methoxy tetrahydrofuran | positive | 409 | 150-920 | 5-35 | 36 | 210 | 20 |
| cyclopentyl fentanyl | positive | 378 | 150-890 | 5-39 | 40 | 210 | 50 |
| thiophene fentanyl | positive | 392 | 150-920 | 5-37 | 38 | 210 | 50 |
| 1-phenethyl-4-piperidone | positive | 204 | 150-500 | 5-76 | 77 | 220 | 20 |
| 1-phenethyl-N-phenylpiperidin-4-amine | positive | 281 | 150-670 | 5-55 | 56 | 230 | 20 | wherein the spotting plate is a triangular paper substrate.

2. The method for rapid on-site detection of fentanyl analogs using a miniature mass spectrometer according to claim 1, wherein: step (2) specifically comprises the following steps: transferring 1-3 μL of liquid sample or 1-3 μg of powder sample to the spotting plate, depositing 5-10 μL of the 3-nitrobenzonitrile solution in acetonitrile at a concentration of 100 μg/μL on the sample, and exposing to air for 10-30 seconds to form a crystalline mixture.

3. The method for rapid on-site detection of fentanyl analogs using a miniature mass spectrometer according to claim 2, wherein: in step (3), the crystalline mixture on the spotting plate was placed in close proximity to the inlet of the miniature mass spectrometer for 1-5 seconds, and the crystalline mixture was expected to produce charged particles upon sublimation due to the intrinsic vacuum at the inlet aperture of the miniature mass spectrometer.

4. The method for rapid on-site detection of fentanyl analogs using a miniature mass spectrometer according to claim 1, wherein: the base and height of the triangular paper substrate are 1 cm and 1.5 cm, respectively.

* * * * *